United States Patent [19]

Bendig et al.

[11] Patent Number: 5,558,864
[45] Date of Patent: Sep. 24, 1996

[54] HUMANIZED AND CHIMERIC ANTI-EPIDERMAL GROWTH FACTOR RECEPTOR MONOCLONAL ANTIBODIES

[75] Inventors: Mary M. Bendig, London; Catherine A. Kettleborough, Herts; Jose Saldanha, Middlesex, all of United Kingdom

[73] Assignee: Merck Patent Gesellschaft Mit Beschrankter Haftung, Darmstadt, Germany

[21] Appl. No.: 946,421

[22] PCT Filed: Mar. 4, 1992

[86] PCT No.: PCT/EP92/00480

§ 371 Date: Nov. 6, 1992

§ 102(e) Date: Nov. 6, 1992

[87] PCT Pub. No.: WO92/15683

PCT Pub. Date: Sep. 17, 1992

[30] Foreign Application Priority Data

Mar. 6, 1991 [EP] European Pat. Off. ............ 911933892

[51] Int. Cl.⁶ .................................................. A61K 35/16
[52] U.S. Cl. .................... 424/133.1; 530/387.3; 530/388.22; 530/867; 424/130.1; 424/143.1; 436/501; 536/23.53
[58] Field of Search .............................. 424/85.8, 143.1, 424/133.1; 530/867, 387.3, 388.22, 330, 329, 328, 327, 326, 325, 324; 436/501; 435/69.7, 70.21, 71.1, 252.3, 320.1, 240.27; 536/23.53

[56] References Cited

FOREIGN PATENT DOCUMENTS 0239400 9/1987 European Pat. Off. ........ C12N 15/00
0328404 8/1989 European Pat. Off. ..... A61K 39/395

OTHER PUBLICATIONS

Harris et al TibTech 11:42–46 1993.
Kabat Sequences of Proteins of Immunological Intent 4th Ed p. 106 1987.
Rechavi et al PNAS 80:8555–859 1983.
Rodeck et al Cancer Research 47:3692–3696 1987.
Cunningham et al TibTech 10 1992.
Tramontano et al., J. of Mol. Biol., vol. 215, No. 1, pp. 175–182 (Sep. 5, 1990).
Murthy et al., Arch Biochem. Biophys., vol. 252, No. 2, pp. 549–560 (Feb. 1, 1987).
Verhoeyen et al., Science, vol. 239, pp. 1534–1536 (Mar. 25, 1988).
Rodeck et al., J. Cell. Biochem., vol. 44, No. 2, pp. 69–79 (Oct. 1990).
Queen et al., Proc. Nat'l Acad. Sci. USA, vol. 86, pp. 10029–10033 (Dec. 1989).
Kettleborough et al., Protein Eng., vol. 4, No. 7, pp. 773–783 (Oct. 1991).

*Primary Examiner*—Donald E. Adams
*Attorney, Agent, or Firm*—Millen, White, Zelano, & Branigan, P.C.

[57] ABSTRACT

Humanized and chimeric anti-epidermal growth factor receptor (anti-EGF-R) monoclonal antibodies are disclosed, comprising an artificial modified consensus sequence for the heavy chain of the framework region of the variable region of a human immunoglobulin. Corresponding humanized and chimeric monoclonal antibodies which bind to epitopes of the epidermal growth factor receptor (EGF-R) having specific amino acid sequences in the hypervariable regions responsible for EGF-R binding are also disclosed. These antibodies are therapeutically and diagnostically useful.

22 Claims, 12 Drawing Sheets

FIG. 2

Panel A:

```
5'--------CGAGCTCGG-CTGAGCACACAGGACCTCACCATG GGT TGG AGC TAT  45
   pUC18----->-3'-GACTCGTGTGTCCTGGAGTGGTACCCA-----5'
              5'-CTCCAAGCTTGACCTCACCATGG-3'
                    ▲
                  HindIII                   Met Gly Trp Ser Tyr
```

| | | | | | | | | | | | | | | |
|---|---|---|---|---|---|---|---|---|---|---|---|---|---|---|
| ATC | ATC | CTC | TTT | TTG | GTA | GCA | ACA | GCT | ACA | GAT | GTC | CAC | TCC | CAG  90 |
| Ile | Ile | Leu | Phe | Leu | Val | Ala | Thr | Ala | Thr | Asp | Val | His | Ser | Gln |
| GTC | CAG | CTG | CAA | CAA | CCT | GGG | GCT | GAA | CTG | GTG | AAG | CCT | GGG | GCT 135 |
| Val | Gln | Leu | Gln | Gln | Pro | Gly | Ala | Glu | Leu | Val | Lys | Pro | Gly | Ala |
| TCA | GTG | AAG | TTG | TCC | TGC | AAG | GCT | TCC | GGC | TAC | ACC | TTC | ACC | AGC 180 |
| Ser | Val | Lys | Leu | Ser | Cys | Lys | Ala | Ser | Gly | Tyr | Thr | Phe | Thr(Ser |
| CAC | TGG | ATG | CAC | TGG | GTG | AAG | CAG | AGG | GCT | GGA | CAA | GGC | CTT | GAG 225 |
| His | Trp | Met | His)Trp | Val | Lys | Gln | Arg | Ala | Gly | Gln | Gly | Leu | Glu |
| TGG | ATC | GGA | GAG | TTT | AAT | CCC | AGC | AAC | GGC | CGT | ACT | AAC | TAC | AAT 270 |
| Trp | Ile | Gly(Glu | Phe | Asn | Pro | Ser | Asn | Gly | Arg | Thr | Asn | Tyr | Asn |
| GAG | AAA | TTC | AAG | AGC | AAG | GCC | ACA | CTG | ACT | GTA | GAC | AAA | TCC | TCC 315 |
| Glu | Lys | Phe | Lys | Ser)Lys | Ala | Thr | Leu | Thr | Val | Asp | Lys | Ser | Ser |
| AGC | ACA | GCC | TAC | ATG | CAA | CTC | AGC | AGC | CTG | ACA | TCT | GAG | GAC | TCT 360 |
| Ser | Thr | Ala | Tyr | Met | Gln | Leu | Ser | Ser | Leu | Thr | Ser | Glu | Asp | Ser |
| GCG | GTC | TAT | TAC | TGT | GCC | AGT | CGG | GAC | TAT | GAT | TAC | GAC | GGA | CGG 405 |
| Ala | Val | Tyr | Tyr | Cys | Ala | Ser(Arg | Asp | Tyr | Asp | Tyr | Asp | Gly | Arg |

```
                                  3'-AG TGT CAG AGG AGT
TAC TTT GAC TAC TGG GGC CAA GGC ACC ACT CTC ACA GTC TCC TCA  450
Tyr Phe Asp Tyr)Trp Gly Gln Gly Thr Thr Leu Thr Val Ser Ser
                  BamHI
CCACTCACCTAGGTT-5'                        <-----pUC18
GCCAAAACAACACCCCATCGGTCTATCCACTGGAT-TCCTCTAGAGTCGACC---3'   501
```

Panel B:

```
    ---pUC18-------->
5'----TTCGAGCTCGGTACCC-ACAAAATG GAT TTT CAA GTG CAG ATT TTC  45
3'----AAGCTCGAGCCATGGG-TGTTTTAC CTA AAA GTT CAC GTC--5'
           5'-AGAAAGCTT-CCACCATG GAT TTT CAA GTG-3'
                    ▲
                  HindIII       Met Asp Phe Gln Val Gln Ile Phe
```

| | | | | | | | | | | | | | | |
|---|---|---|---|---|---|---|---|---|---|---|---|---|---|---|
| AGC | TTC | CTG | CTA | ATC | AGT | GCC | TCA | GTC | ATA | CTG | TCC | AGA | GGA | CAA  90 |
| Ser | Phe | Leu | Leu | Ile | Ser | Ala | Ser | Val | Ile | Leu | Ser | Arg | Gly | Gln |
| ATT | GTT | CTC | ACC | CAG | TCT | CCA | GCA | ATC | ATG | TCT | GCA | TCT | CCA | GGG 135 |
| Ile | Val | Leu | Thr | Gln | Ser | Pro | Ala | Ile | Met | Ser | Ala | Ser | Pro | Gly |
| GAG | AAG | GTC | ACT | ATG | ACC | TGC | AGT | GCC | AGC | TCA | AGT | GTA | ACT | TAC 180 |
| Glu | Lys | Val | Thr | Met | Thr | Cys(Ser | Ala | Ser | Ser | Ser | Val | Thr | Tyr |
| ATG | TAT | TGG | TAC | CAG | CAG | AAG | CCA | GGA | TCC | TCC | CCC | AGA | CTC | CTG 225 |
| Met | Tyr)Trp | Tyr | Gln | Gln | Lys | Pro | Gly | Ser | Ser | Pro | Arg | Leu | Leu |
| ATT | TAT | GAC | ACA | TCC | AAC | CTG | GCT | TCT | GGA | GTC | CCT | GTT | CGT | TTC 270 |
| Ile | Tyr(Asp | Thr | Ser | Asn | Leu | Ala | Ser)Gly | Val | Pro | Val | Arg | Phe |
| AGT | GGC | AGT | GGG | TCT | GGG | ACC | TCT | TAC | TCT | CTC | ACA | ATC | AGC | CGA 315 |
| Ser | Gly | Ser | Gly | Ser | Gly | Thr | Ser | Tyr | Ser | Leu | Thr | Ile | Ser | Arg |
| ATG | GAG | GCT | GAA | GAT | GCT | GCC | ACT | TAT | TAC | TGC | CAG | CAG | TGG | AGT 360 |
| Met | Glu | Ala | Glu | Asp | Ala | Ala | Thr | Tyr | Tyr | Cys(Gln | Gln | Trp | Ser |

```
                                     3'-C AAC CTT TAT TTT
AGT CAC ATA TTC ACG TTC GGC TCG GGG ACA AAG TTG GAA ATA AAA  405
Ser His Ile Phe Thr)Phe Gly Ser Gly Thr Lys Leu Glu Ile Lys
GCACTCATCTAGATG-5'  BglII                         <-- pUC18
CGGGCTGATGCTGCACCAACTGTATGGATCTTCCCACCATCCAGGATCC-GGGGATCC-3' 462
```

FIG. 3

```
       HindIII
5'--AAGCTTGCCGCCACC ATG GAC TGG ACC TGG CGC GTG TTT TGC CTG   45
                    Met Asp Trp Thr Trp Arg Val Phe Cys Leu CTC GCC GTG GCT CCT GGG GCC CAC AGC CAG GTG CAA CTA GTG CAG   90
Leu Ala Val Ala Pro Gly Ala His Ser Gln Val Gln Leu Val Gln TCC GGC GCC GAA GTG AAG AAA CCC GGT GCT TCC GTG AAG GTG AGC  135
Ser Gly Ala Glu Val Lys Lys Pro Gly Ala Ser Val Lys Val Ser TGT AAA GCT AGC GGT TAT ACC TTC TCT TCC CAC TGG ATG CAT TGG  180
Cys Lys Ala Ser Gly Tyr Thr Phe Ser(Ser His Trp Met His)Trp GTT AGA CAG GCC CCA GGC CAA GGG CTC GAG TGG GTG GGC GAG TTC  225
Val Arg Gln Ala Pro Gly Gln Gly Leu Glu Trp Val Gly(Glu Phe AAC CCT TCA AAT GGC CGG ACA AAT TAT AAC GAG AAG TTT AAG AGC  270
Asn Pro Ser Asn Gly Arg Thr Asn Tyr Asn Glu Lys Phe Lys Ser)

AGG GTT ACC ATG ACC TTG GAC ACC TCT ACA AAC ACC GCC TAC ATG  315
Arg Val Thr Met Thr Leu Asp Thr Ser Thr Asn Thr Ala Tyr Met

GAA CTG TCC AGC CTG CGC TCC GAG GAC ACT GCA GTC TAC TAC TGC  360
Glu Leu Ser Ser Leu Arg Ser Glu Asp Thr Ala Val Tyr Tyr Cys

GCC TCA CGG GAT TAC GAT TAC GAT GGC AGA TAC TTC GAC TAT TGG  405
Ala Ser(Arg Asp Tyr Asp Tyr Asp Gly Arg Tyr Phe Asp Tyr)Trp
                                              BamHI EcoRI
GGA CAG GGT ACC CTT GTC ACC GTC AGT TCA GGTGAGTGGATCCGAATTC  454
Gly Gln Gly Thr Leu Val Thr Val Ser Ser
```

FIG. 4A

Panel A:

| | | |
|---|---|---|
| VL425 | Gln-Ile-Val-Leu-Thr-Gln-Ser-Pro-Ala-Ile- | |
| RVLa425 | Asp-Ile-Gln-Met-Thr-Gln-Ser-Pro-Ser-Ser- | |
| RVLb425 | ---------- | |
| VL425 | Met-Ser-Ala-Ser-Pro-Gly-Glu-Lys-Val-Thr- | FR-1 |
| RVLa425 | Leu-Ser-Ala-Ser-Val-Gly-Asp-Arg-Val-Thr- | |
| RVLb425 | ---------- | |
| VL425 | Met-Thr-Cys | |
| RVLa425 | Ile-Thr-Cys | |
| RVLb425 | ---------- | |

| | | |
|---|---|---|
| VL425 | Ser-Ala-Ser-Ser-Ser-Val-Thr-Tyr-Met-Tyr | |
| RVLa425 | Ser-Ala-Ser-Ser-Ser-Val-Thr-Tyr-Met-Tyr | CDR-1 |
| RVLb425 | ---------- | |

| | | |
|---|---|---|
| VL425 | Trp-Tyr-Gln-Gln-Lys-Pro-Gly-Ser-Ser-Pro- | |
| RVLa425 | Trp-Tyr-Gln-Gln-Lys-Pro-Gly-Lys-Ala-Pro- | |
| RVLb425 | ---------- | FR-2 |
| VL425 | Arg-Leu-Leu-Ile-Tyr | |
| RVLa425 | Lys-Leu-Leu-Ile-Tyr | |
| RVLb425 | ---------- | |

| | | |
|---|---|---|
| VL425 | Asp-Thr-Ser-Asn-Leu-Ala-Ser | |
| RVLa425 | Asp-Thr-Ser-Asn-Leu-Ala-Ser | CDR-2 |
| RVLb425 | ---------- | |

| | | |
|---|---|---|
| VL425 | Gly-Val-Pro-Val-Arg-Phe-Ser-Gly-Ser-Gly- | |
| RVLa425 | Gly-Val-Pro-Ser-Arg-Phe-Ser-Gly-Ser-Gly- | |
| RVLb425 | ---------- | |
| VL425 | Ser-Gly-Thr-Ser-Tyr-Ser-Leu-Thr-Ile-Ser- | FR-3 |
| RVLa425 | Ser-Gly-Thr-Asp-Phe-Thr-Phe-Thr-Ile-Ser- | |
| RVLb425 | ----------------Tyr------------------ | |
| VL425 | Arg-Met-Glu-Ala-Glu-Asp-Ala-Ala-Thr-Tyr-Tyr-Cys | |
| RVLa425 | Ser-Leu-Gln-Pro-Glu-Asp-Ile-Ala-Thr-Tyr-Tyr-Cys | |
| RVLb425 | ---------- | |

| | | |
|---|---|---|
| VL425 | Gln-Gln-Trp-Ser-Ser-His-Ile-Phe-Thr | |
| RVLa425 | Gln-Gln-Trp-Ser-Ser-His-Ile-Phe-Thr | CDR-3 |
| RVLb425 | ---------- | |

| | | |
|---|---|---|
| VL425 | Phe-Gly-Ser-Gly-Thr-Lys-Leu-Glu-Ile-Lys | |
| RVLa425 | Phe-Gly-Gln-Gly-Thr-Lys-Val-Glu-Ile-Lys | FR-4 |
| RVLb425 | ---------- | |

FIG. 4B

Panel B:

| | | |
|---|---|---|
| VH 425 | Gln-Val-Gln-Leu-Gln-Gln-Pro-Gly-Ala-Glu- | |
| RVH a-d, f425 | Gln-Val-Gln-Leu-Val-Gln-Ser-Gly-Ala-Glu- | |
| RVH e, g-i425 | ------------------------------------ | |
| VH 425 | Leu-Val-Lys-Pro-Gly-Ala-Ser-Val-Lys-Leu- | FR-1 |
| RVH a-d, f425 | Val-Lys-Lys-Pro-Gly-Ala-Ser-Val-Lys-Val- | |
| RVH e, g-i425 | ------------------------------------ | |
| VH 425 | Ser-Cys-Lys-Ala-Ser-Gly-Tyr-Thr-Phe-Thr | |
| RVH a-d, f425 | Ser-Cys-Lys-Ala-Ser-Gly-Tyr-Thr-Phe-Ser | |
| RVH e, g-i425 | ----------------------------------Thr | |

| | | |
|---|---|---|
| VH 425 | Ser-His-Trp-Met-His | CDR-1 |
| RVH a-i425 | Ser-His-Trp-Met-His | |

| | | |
|---|---|---|
| VH 425 | Trp-Val-Lys-Gln-Arg-Ala-Gly-Gln-Gly-Leu- | |
| RVH a-c, h, i425 | Trp-Val-Arg-Gln-Ala-Pro-Gly-Gln-Gly-Leu- | |
| RVH d-g425 | ------------------------------------ | |
| VH 425 | Glu-Trp-Ile-Gly | FR-2 |
| RVH a-c, h, i425 | Glu-Trp-Val-Gly | |
| RVH d-g425 | --------Ile---- | |

| | | |
|---|---|---|
| VH 425 | Glu-Phe-Asn-Pro-Ser-Asn-Gly-Arg-Thr-Asn- | |
| RVH a-i425 | Glu-Phe-Asn-Pro-Ser-Asn-Gly-Arg-Thr-Asn- | |
| VH 425 | Tyr-Asn-Glu-Lys-Phe-Lys-Ser | CDR-2 |
| RVH a-i425 | Tyr-Asn-Glu-Lys-Phe-Lys-Ser | |

| | | |
|---|---|---|
| VH 425 | Lys-Ala-Thr-Leu-Thr-Val-Asp-Lys-Ser-Ser- | |
| RVH a, d, e425 | Arg-Val-Thr-Met-Thr-Leu-Asp-Thr-Ser-Thr- | |
| RVH b, h425 | --------------------Val----------------- | |
| RVH c, f, g, i425 | Lys-Ala-------------Val----------------- | |
| VH 425 | Ser-Thr-Ala-Tyr-Met-Gln-Leu-Ser-Ser-Leu- | |
| RVH a, d, e425 | Asn-Thr-Ala-Tyr-Met-Glu-Leu-Ser-Ser-Leu- | FR-3 |
| RVH a, d, e425 | ------------------------------------ | |
| RVH c, f, g, i425 | ------------------------------------ | |
| VH 425 | Thr-Ser-Glu-Asp-Ser-Ala-Val-Tyr-Tyr-Cys-Ala-Ser | |
| RVH a, d, e425 | Arg-Ser-Glu-Asp-Thr-Ala-Val-Tyr-Tyr-Cys-Ala-Ser | |
| RVH a, d, e425 | ------------------------------------ | |
| RVH c, f, g, i425 | ------------------------------------ | |

| | | |
|---|---|---|
| VH 425 | Arg-Asp-Tyr-Asp-Tyr-Asp-Gly-Arg-Tyr-Phe-Asp-Tyr | CDR-3 |
| RVH a-i425 | Arg-Asp-Tyr-Asp-Tyr-Asp-Gly-Arg-Tyr-Phe-Asp-Tyr | |

| | | |
|---|---|---|
| VH 425 | Trp-Gly-Gln-Gly-Thr-Thr-Leu-Thr-Val-Ser-Ser | FR-4 |
| RVH a-i425 | Trp-Gly-Gln-Gly-Thr-Leu-Val-Thr-Val-Ser-Ser | |

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:1:

```
Ser  Ala  Ser  Ser  Ser  Val  Thr  Tyr  Met  Tyr
1                   5                        10
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:2:

```
Asp Thr Ser Asn Leu Ala Ser
1               5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:3:

```
Gln Gln Trp Ser Ser His Ile Phe Thr
1               5
```

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:4:

```
Ser His Trp Met His
1               5
```

( 2 ) INFORMATION FOR SEQ ID NO:5:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:5:

```
Glu Phe Asn Pro Ser Asn Gly Arg Thr Asn Tyr Asn Glu Lys Phe Lys
1               5                   10                  15
Ser
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:6:

```
Arg Asp Tyr Asp Tyr Asp Gly Arg Tyr Phe Asp Tyr
1               5                   10
```

( 2 ) INFORMATION FOR SEQ ID NO:7:

( i ) SEQUENCE CHARACTERISTICS:
        ( A ) LENGTH: 23 amino acids
        ( B ) TYPE: amino acid
        ( D ) TOPOLOGY: linear ( x i ) SEQUENCE DESCRIPTION: SEQ ID NO:7:

```
Asp Ile Gln Met Thr Gln Ser Pro Ser Ser Leu Ser Ala Ser Val Gly
1               5                   10                  15
```

Asp Arg Val Thr Ile Thr Cys
                20

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:8:

Trp Tyr Gln Gln Lys Pro Gly Lys Ala Pro Lys Leu Leu Ile Tyr
1               5                   10                  15

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( D ) TOPOLOGY: linear ( i x ) FEATURE:
        ( A ) NAME/KEY: Region
        ( B ) LOCATION: 15
        ( D ) OTHER INFORMATION: /note="Amino acid 15 can be Tyr,
                Phe, Trp or His."

( x i ) SEQUENCE DESCRIPTION: SEQ ID NO:9:

Gly Val Pro Ser Arg Phe Ser Gly Ser Gly Ser Gly Thr Asp Xaa Thr
1               5                   10                  15

Phe Thr Ile Ser Ser Leu Gln Pro Glu Asp Ile Ala Thr Tyr Tyr Cys
                20                  25                  30

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:10:

Phe Gly Gln Gly Thr Lys Val Glu Ile Lys
1               5                   10

( 2 ) INFORMATION FOR SEQ ID NO:11:

( i ) SEQUENCE CHARACTERISTICS:
        ( A ) LENGTH: 30 amino acids
        ( B ) TYPE: amino acid
        ( D ) TOPOLOGY: linear ( i x ) FEATURE:
        ( A ) NAME/KEY: Region
        ( B ) LOCATION: 30
        ( D ) OTHER INFORMATION: /note="Amino acid 30 can be Thr or
                Ser."

( x i ) SEQUENCE DESCRIPTION: SEQ ID NO:11:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa
                20                  25                  30

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( D ) TOPOLOGY: linear ( i x ) FEATURE:
    ( A ) NAME/KEY: Region
    ( B ) LOCATION: 3
    ( D ) OTHER INFORMATION: /note="Amino acid 3 can be Arg
        or His."

( i x ) FEATURE:
    ( A ) NAME/KEY: Region
    ( B ) LOCATION: 5
    ( D ) OTHER INFORMATION: /note="Amino acid 5 can be Ala,
        Lys or His."

( i x ) FEATURE:
    ( A ) NAME/KEY: Region
    ( B ) LOCATION: 6
    ( D ) OTHER INFORMATION: /note="Amino acid 6 can be Pro or
        Val."

( i x ) FEATURE:
    ( A ) NAME/KEY: Region
    ( B ) LOCATION: 13
    ( D ) OTHER INFORMATION: /note="Amino acid 13 can be Ile,
        Val or Leu."

( x i ) SEQUENCE DESCRIPTION: SEQ ID NO:12:

```
Trp  Val  Xaa  Gln  Xaa  Xaa  Gly  Gln  Gly  Leu  Glu  Trp  Xaa  Gly
 1              5                        10
```

( 2 ) INFORMATION FOR SEQ ID NO:13:

( i ) SEQUENCE CHARACTERISTICS:
        ( A ) LENGTH: 32 amino acids
        ( B ) TYPE: amino acid
        ( D ) TOPOLOGY: linear ( i x ) FEATURE:
        ( A ) NAME/KEY: Region
        ( B ) LOCATION: 1
        ( D ) OTHER INFORMATION: /note="Amino acid 1 can be Lys,
            Arg or His."

( i x ) FEATURE:
        ( A ) NAME/KEY: Region
        ( B ) LOCATION: 2
        ( D ) OTHER INFORMATION: /note="Amino acid 2 can be Ala,
            Val, Pro or Gly."

( i x ) FEATURE:
        ( A ) NAME/KEY: Region
        ( B ) LOCATION: 6
        ( D ) OTHER INFORMATION: /note="Amino acid 6 can be Val,
            Ala, Pro or Gly."

( i x ) FEATURE:
        ( A ) NAME/KEY: Region
        ( B ) LOCATION: 16
        ( D ) OTHER INFORMATION: /note="Amino acid 16 can be Glu or
            Asn."

( x i ) SEQUENCE DESCRIPTION: SEQ ID NO:13:

```
Xaa  Xaa  Thr  Met  Thr  Xaa  Asp  Thr  Ser  Thr  Asn  Thr  Ala  Tyr  Met  Xaa
 1              5                        10                       15
Leu  Ser  Ser  Leu  Arg  Ser  Glu  Asp  Thr  Ala  Val  Tyr  Tyr  Cys  Ala  Ser
              20                       25                       30
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:14:

Trp Gly Gln Gly Thr Leu Val Thr Val Ser Ser
1               5                   10

( 2 ) INFORMATION FOR SEQ ID NO:15:

( i ) SEQUENCE CHARACTERISTICS:
      ( A ) LENGTH: 23 amino acids
      ( B ) TYPE: amino acid
      ( D ) TOPOLOGY: linear ( x i ) SEQUENCE DESCRIPTION: SEQ ID NO:15:

Gln Ile Val Leu Thr Gln Ser Pro Ala Ile Met Ser Ala Ser Pro Gly
1               5                   10                  15

Glu Lys Val Thr Met Thr Cys
            20

( 2 ) INFORMATION FOR SEQ ID NO:16:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:16:

Trp Tyr Gln Gln Lys Pro Gly Ser Ser Pro Arg Leu Leu Ile Tyr
1               5                   10                  15

( 2 ) INFORMATION FOR SEQ ID NO:17:

( i ) SEQUENCE CHARACTERISTICS:
      ( A ) LENGTH: 32 amino acids
      ( B ) TYPE: amino acid
      ( D ) TOPOLOGY: linear ( x i ) SEQUENCE DESCRIPTION: SEQ ID NO:17:

Gly Val Pro Val Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30

( 2 ) INFORMATION FOR SEQ ID NO:18:

( i ) SEQUENCE CHARACTERISTICS:
      ( A ) LENGTH: 10 amino acids
      ( B ) TYPE: amino acid
      ( D ) TOPOLOGY: linear ( x i ) SEQUENCE DESCRIPTION: SEQ ID NO:18:

Phe Gly Ser Gly Thr Lys Leu Glu Ile Lys
1               5                   10

( 2 ) INFORMATION FOR SEQ ID NO:19:

( i ) SEQUENCE CHARACTERISTICS:
      ( A ) LENGTH: 30 amino acids
      ( B ) TYPE: amino acid
      ( D ) TOPOLOGY: linear ( x i ) SEQUENCE DESCRIPTION: SEQ ID NO:19:

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr
            20                  25                  30

( 2 ) INFORMATION FOR SEQ ID NO:20:

( i ) SEQUENCE CHARACTERISTICS:
   ( A ) LENGTH: 14 amino acids
   ( B ) TYPE: amino acid
   ( D ) TOPOLOGY: linear ( x i ) SEQUENCE DESCRIPTION: SEQ ID NO:20:

Trp Val Lys Gln Arg Ala Gly Gln Gly Leu Glu Trp Ile Gly
1               5                   10

( 2 ) INFORMATION FOR SEQ ID NO:21:

( i ) SEQUENCE CHARACTERISTICS:
      ( A ) LENGTH: 32 amino acids
      ( B ) TYPE: amino acid
      ( D ) TOPOLOGY: linear ( x i ) SEQUENCE DESCRIPTION: SEQ ID NO:21:

Lys Ala Thr Leu Thr Val Asp Lys Ser Ser Ser Thr Ala Tyr Met Gln
1               5                   10                  15

Leu Ser Ser Leu Thr Ser Glu Asp Ser Ala Val Tyr Tyr Cys Ala Ser
              20                  25                  30

( 2 ) INFORMATION FOR SEQ ID NO:22:

( i ) SEQUENCE CHARACTERISTICS:
      ( A ) LENGTH: 11 amino acids
      ( B ) TYPE: amino acid
      ( D ) TOPOLOGY: linear ( x i ) SEQUENCE DESCRIPTION: SEQ ID NO:22:

Trp Gly Gln Gly Thr Thr Leu Thr Val Ser Ser
1               5                   10

( 2 ) INFORMATION FOR SEQ ID NO:23:

( i ) SEQUENCE CHARACTERISTICS:
      ( A ) LENGTH: 501 base pairs
      ( B ) TYPE: nucleic acid
      ( C ) STRANDEDNESS: double
      ( D ) TOPOLOGY: linear ( x i ) SEQUENCE DESCRIPTION: SEQ ID NO:23:

| | | | | | |
|---|---|---|---|---|---|
| CGAGCTCGGC | TGAGCACACA | GGACCTCACC | ATGGGTTGGA | GCTATATCAT | CCTCTTTTTG | 60 |
| GTAGCAACAG | CTACAGATGT | CCACTCCCAG | GTCCAGCTGC | AACAACCTGG | GGCTGAACTG | 120 |
| GTGAAGCCTG | GGCTTCAGT  | GAAGTTGTCC | TGCAAGGCTT | CCGGCTACAC | CTTCACCAGC | 180 |
| CACTGGATGC | ACTGGGTGAA | GCAGAGGGCT | GGACAAGGCC | TTGAGTGGAT | CGGAGAGTTT | 240 |
| AATCCCAGCA | ACGGCCGTAC | TAACTACAAT | GAGAAATTCA | AGAGCAAGGC | CACACTGACT | 300 |
| GTAGACAAAT | CCTCCAGCAC | AGCCTACATG | CAACTCAGCA | GCCTGACATC | TGAGGACTCT | 360 |
| GCGGTCTATT | ACTGTGCCAG | TCGGGACTAT | GATTACGACG | GACGGTACTT | TGACTACTGG | 420 |
| GGCCAAGGCA | CCACTCTCAC | AGTCTCCTCA | GCCAAAACAA | CACCCCATCG | GTCTATCCAC | 480 |
| TGGATTCCTC | TAGAGTCGAC | C | | | | 501 |

( 2 ) INFORMATION FOR SEQ ID NO:24:

( i ) SEQUENCE CHARACTERISTICS:
      ( A ) LENGTH: 140 amino acids
      ( B ) TYPE: amino acid
      ( D ) TOPOLOGY: linear ( x i ) SEQUENCE DESCRIPTION: SEQ ID NO:24:

Met Gly Trp Ser Tyr Ile Ile Leu Phe Leu Val Ala Thr Ala Thr Asp
1               5                   10                  15

| | | | | | | | | | | | | | | |
|---|---|---|---|---|---|---|---|---|---|---|---|---|---|---|
|Val|His|Ser|Gln|Val|Gln|Leu|Gln|Gln|Pro|Gly|Ala|Glu|Leu|Val|Lys|
| | | |20| | | |25| | | | |30| | |
|Pro|Gly|Ala|Ser|Val|Lys|Leu|Ser|Cys|Lys|Ala|Ser|Gly|Tyr|Thr|Phe|
| | |35| | | |40| | | | |45| | | |
|Thr|Ser|His|Trp|Met|His|Trp|Val|Lys|Gln|Arg|Ala|Gly|Gln|Gly|Leu|
| |50| | | |55| | | | |60| | | | |
|Glu|Trp|Ile|Gly|Glu|Phe|Asn|Pro|Ser|Asn|Gly|Arg|Thr|Asn|Tyr|Asn|
|65| | | |70| | | | |75| | | | |80|
|Glu|Lys|Phe|Lys|Ser|Lys|Ala|Thr|Leu|Thr|Val|Asp|Lys|Ser|Ser|Ser|
| | | |85| | | |90| | | | |95| | |
|Thr|Ala|Tyr|Met|Gln|Leu|Ser|Ser|Leu|Thr|Ser|Glu|Asp|Ser|Ala|Val|
| | |100| | | |105| | | | |110| | | |
|Tyr|Tyr|Cys|Ala|Ser|Arg|Asp|Tyr|Asp|Tyr|Asp|Gly|Arg|Tyr|Phe|Asp|
| |115| | | |120| | | | |125| | | | |
|Tyr|Trp|Gly|Gln|Gly|Thr|Thr|Leu|Thr|Val|Ser|Ser| | | | |
| |130| | | |135| | | | |140| | | | | |

( 2 ) INFORMATION FOR SEQ ID NO:25:

( i ) SEQUENCE CHARACTERISTICS:
        ( A ) LENGTH: 462 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:25:

```
TTCGAGCTCG GTACCCACAA AATGGATTTT CAAGTGCAGA TTTTCAGCTT CCTGCTAATC      60
AGTGCCTCAG TCATACTGTC CAGAGGACAA ATTGTTCTCA CCCAGTCTCC AGCAATCATG     120
TCTGCATCTC CAGGGGAGAA GGTCACTATG ACCTGCAGTG CCAGCTCAAG TGTAACTTAC     180
ATGTATTGGT ACCAGCAGAA GCCAGGATCC TCCCCCAGAC TCCTGATTTA TGACACATCC     240
AACCTGGCTT CTGGAGTCCC TGTTCGTTTC AGTGGCAGTG GGTCTGGGAC CTCTTACTCT     300
CTCACAATCA GCCGAATGGA GGCTGAAGAT GCTGCCACTT ATTACTGCCA GCAGTGGAGT     360
AGTCACATAT TCACGTTCGG CTCGGGGACA AAGTTGGAAA TAAAACGGGC TGATGCTGCA     420
CCAACTGTAT GGATCTTCCC ACCATCCAGG ATCCGGGGAT CC                       462
```

( 2 ) INFORMATION FOR SEQ ID NO:26:

( i ) SEQUENCE CHARACTERISTICS:
        ( A ) LENGTH: 128 amino acids
        ( B ) TYPE: amino acid
        ( D ) TOPOLOGY: linear ( x i ) SEQUENCE DESCRIPTION: SEQ ID NO:26:

| | | | | | | | | | | | | | | |
|---|---|---|---|---|---|---|---|---|---|---|---|---|---|---|
|Met|Asp|Phe|Gln|Val|Gln|Ile|Phe|Ser|Phe|Leu|Leu|Ile|Ser|Ala|Ser|
|1| | | |5| | | |10| | | | |15| | |
|Val|Ile|Leu|Ser|Arg|Gly|Gln|Ile|Val|Leu|Thr|Gln|Ser|Pro|Ala|Ile|
| | | |20| | | |25| | | | |30| | | |
|Met|Ser|Ala|Ser|Pro|Gly|Glu|Lys|Val|Thr|Met|Thr|Cys|Ser|Ala|Ser|
| | |35| | | |40| | | | |45| | | | |
|Ser|Ser|Val|Thr|Tyr|Met|Tyr|Trp|Tyr|Gln|Gln|Lys|Pro|Gly|Ser|Ser|
| |50| | | |55| | | | |60| | | | | |
|Pro|Arg|Leu|Leu|Ile|Tyr|Asp|Thr|Ser|Asn|Leu|Ala|Ser|Gly|Val|Pro|
|65| | | |70| | | | |75| | | | |80| |
|Val|Arg|Phe|Ser|Gly|Ser|Gly|Ser|Gly|Thr|Ser|Tyr|Ser|Leu|Thr|Ile|
| | | |85| | | |90| | | | |95| | | |

```
            Ser  Arg  Met  Glu  Ala  Glu  Asp  Ala  Ala  Thr  Tyr  Tyr  Cys  Gln  Gln  Trp
                           100                 105                           110

Ser  Ser  His  Ile  Phe  Thr  Phe  Gly  Ser  Gly  Thr  Lys  Leu  Glu  Ile  Lys
                      115                 120                      125
```

( 2 ) INFORMATION FOR SEQ ID NO:27:

( i ) SEQUENCE CHARACTERISTICS:
        ( A ) LENGTH: 454 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:27:

```
AAGCTTGCCG  CCACCATGGA  CTGGACCTGG  CGCGTGTTTT  GCCTGCTCGC  CGTGGCTCCT      60

GGGGCCCACA  GCCAGGTGCA  ACTAGTGCAG  TCCGGCGCCG  AAGTGAAGAA  ACCCGGTGCT     120

TCCGTGAAGG  TGAGCTGTAA  AGCTAGCGGT  TATACCTTCT  CTTCCCACTG  GATGCATTGG     180

GTTAGACAGG  CCCCAGGCCA  AGGGCTCGAG  TGGGTGGGCG  AGTTCAACCC  TTCAAATGGC     240

CGGACAAATT  ATAACGAGAA  GTTTAAGAGC  AGGGTTACCA  TGACCTTGGA  CACCTCTACA     300

AACACCGCCT  ACATGGAACT  GTCCAGCCTG  CGCTCCGAGG  ACACTGCAGT  CTACTACTGC     360

GCCTCACGGG  ATTACGATTA  CGATGGCAGA  TACTTCGACT  ATTGGGGACA  GGGTACCCTT     420

GTCACCGTCA  GTTCAGGTGA  GTGGATCCGA  ATTC                                   454
```

( 2 ) INFORMATION FOR SEQ ID NO:28:

( i ) SEQUENCE CHARACTERISTICS:
        ( A ) LENGTH: 140 amino acids
        ( B ) TYPE: amino acid
        ( D ) TOPOLOGY: linear ( x i ) SEQUENCE DESCRIPTION: SEQ ID NO:28:

```
            Met  Asp  Trp  Thr  Trp  Arg  Val  Phe  Cys  Leu  Leu  Ala  Val  Ala  Pro  Gly
            1                  5                       10                           15

Ala  His  Ser  Gln  Val  Gln  Leu  Val  Gln  Ser  Gly  Ala  Glu  Val  Lys  Lys
                           20                      25                           30

Pro  Gly  Ala  Ser  Val  Lys  Val  Ser  Cys  Lys  Ala  Ser  Gly  Tyr  Thr  Phe
                           35                      40                           45

Ser  Ser  His  Trp  Met  His  Trp  Val  Arg  Gln  Ala  Pro  Gly  Gln  Gly  Leu
                 50                      55                      60

Glu  Trp  Val  Gly  Glu  Phe  Asn  Pro  Ser  Asn  Gly  Arg  Thr  Asn  Tyr  Asn
            65                      70                      75                           80

Glu  Lys  Phe  Lys  Ser  Arg  Val  Thr  Met  Thr  Leu  Asp  Thr  Ser  Thr  Asn
                                85                      90                      95

Thr  Ala  Tyr  Met  Glu  Leu  Ser  Ser  Leu  Arg  Ser  Glu  Asp  Thr  Ala  Val
                           100                     105                          110

Tyr  Tyr  Cys  Ala  Ser  Arg  Asp  Tyr  Asp  Tyr  Asp  Gly  Arg  Tyr  Phe  Asp
                      115                     120                     125

Tyr  Trp  Gly  Gln  Gly  Thr  Leu  Val  Thr  Val  Ser  Ser
                 130                     135                     140
```

( 2 ) INFORMATION FOR SEQ ID NO:29:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GTAGGATCCT GGATGGTGGG AAGATG                                    26

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GTAGGATCCA GTGGATAGAC CGATG                                     25

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

CTCCAAGCTT GACCTCACCA TGG                                       23

( 2 ) INFORMATION FOR SEQ ID NO:32:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

TTGGATCCAC TCACCTGAGG AGACTGTGA                                 29

( 2 ) INFORMATION FOR SEQ ID NO:33:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

AGAAAGCTTC CACCATGGAT TTTCAAGTG                                 29

( 2 ) INFORMATION FOR SEQ ID NO:34:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GTAGATCTAC TCACGTTTTA TTTCCAAC                                  28

( 2 ) INFORMATION FOR SEQ ID NO:35:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

ACCATCACCT GTAGTGCCAG CTCAAGTGTA ACTTACATGT ATTGGTACCA GCAG      54

( 2 ) INFORMATION FOR SEQ ID NO:36:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

CTGCTGATCT ACGACACATC CAACCTGGCT TCTGGTGTGC CAAGC    45

( 2 ) INFORMATION FOR SEQ ID NO:37:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

ACCTACTACT GCCAGCAGTG GAGTAGTCAC ATATTCACGT TCGGCCAA    48

( 2 ) INFORMATION FOR SEQ ID NO:38:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

AGCGGTACCG ACTACACCTT CACCATC    27

( 2 ) INFORMATION FOR SEQ ID NO:39:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

ATACCTTCAC ATCCCACTG    19

( 2 ) INFORMATION FOR SEQ ID NO:40:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CGAGTGGATT GGCGAGT    17

( 2 ) INFORMATION FOR SEQ ID NO:41:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

TTTAAGAGCA AGGCTACCAT GACCGTGGAC ACCTCT    36

( 2 ) INFORMATION FOR SEQ ID NO:42:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:42:

CATGACCGTG GACACCTCT                                                                                                    19

HUMANIZED AND CHIMERIC ANTI-EPIDERMAL GROWTH FACTOR RECEPTOR MONOCLONAL ANTIBODIES

TECHNICAL FIELD OF THE INVENTION

The invention relates to new humanized monoclonal antibodies comprising an artificial modified consensus sequence at least of the FRs in the variable region of the heavy chain of human immunoglobulins.

The invention relates, furthermore, to humanized and chimeric monoclonal antibodies which are binding to epitopes of the Epidermal Growth Factor. The invention discloses the amino acid sequences of the responding antigen-binding site for this receptor.

The invention relates to pharmaceutical compositions comprising the said antibodies for the purposes of treating tumors like melanoma, glioma or carcinoma. The said antibodies can be used also for diagnostic applications regarding locating and assessing the said tumors in vitro or in vivo.

The specification relates to several technical terms which are here defined as follows:

"Humanized" antibodies mean antibodies comprising FRs of the variable regions and constant regions of amino acids located in the light and heavy chain which derive from human sources whereas the hypervariable regions derive from non-human sources.

"Chimeric" antibodies mean antibodies comprising variable and hypervariable regions which derive from non-human sources whereas the constant regions derive from human origin.

"FRs" mean the framework regions of an antibody and are found within the variable regions. In these regions a certain alteration of amino acids occurs.

"CDRs" mean the complementarity determining or "hypervariable" regions of an antibody and are found within the variable regions. These regions represent the specific antigen-binding site and show an immense exchange of amino acids. CDRs are primarily responsible for the binding affinity of the antigen.

"Consensus sequence" means a non-naturally occurring amino acid sequence as light or heavy chain variable regions and is used as substitute for the originally present non-human heavy or light chain variable regions. The consensus sequences is synthetic and therefore an artificial sequence of the most common amino acids of a distinct class or subclass or subgroup of heavy or light chains of human immunoglobuins.

"EGF" and "EGFR" mean the Epidermal Growth Factor and its receptor.

"$V_L$" regions mean light chain variable regions.

"$V_H$" regions mean heavy chain variable regions.

BACKGROUND OF THE INVENTION

The murine monoclonal antibody 425 (MAb 425) was raised against the human A431 carcinoma cell line and found to bind to a polypeptide epitope on the external domain of the human epidermal growth factor receptor (EGFR). It was found to inhibit the binding of epidermal growth factor (EGF) at both low and high affinity EGFR sites (Murthy et al., 1987), Enhanced expression of EGFR is found to occur on malignant tissue from a variety of sources thus making MAb 425 a possible agent for the diagnosis and therapeutic treatment of human tumors. Indeed, MAb 425 was found to mediate tumor cytotoxicity in vitro and to suppress tumor cell growth of epidermoid and colorectal carcinoma-derived cell lines in vitro (Rodeck et al., 1987). Radiolabelled MAb 425 has also been shown to bind to xenografts of human malignant gliomas in mice (Takahashi et al., 1987).

EGF is a polypeptide hormone which is mitogenic for epidermal and epithelial cells. When EGF interacts with sensitive cells, it binds to membrane receptors; the receptor EGF complexes cluster and then are internalized in endocytotic vesicles. This is responsible for the phenomenon of "down-regulation". EGF binding induces a tyrosine kinase activity of the receptor molecule and induces synthesis of DNA.

The EGF-receptor is a transmembrane glycoprotein of about 170,000 Daltons (Cohen, 1982). It is the gene product of the c-erb-B proto-oncogene (Downward et al., Nature, Vol. 307, pp. 521–527, 1984). The receptor exists in two kinetic forms: so-called low affinity and high-affinity receptors.

The A431 carcinoma cell line expresses abundant EGF-receptors on its cell surfaces, and thus has been used in many studies to generate anti-EGF-receptor antibodies. However, the receptors on A431 differ from those of other cell types in the carbohydrate moieties attached to the polypeptide. Thus many antibodies raised against A431 membranes are directed against carbohydrates which are not common to all forms of the receptor molecule (e.g. Schreiber, 1983).

Other monoclonal antibodies are reactive with the protein moiety of EGF-receptors. These antibodies display a variety of properties upon binding to EGF-receptors, presumably dependent on the particular portion of the receptor molecule bound, and the isotype of the antibody. Some antibodies mimic some of the effects of EGF (agonists) and some inhibit the effects (antagonists).

Expression of EGF-receptors has been implicated in the progression of tumor growth. The gene for the receptors has been found to be the cellular analogue of the avian viral oncogene v-erb-B (Ulrich, 1984). In addition an association has been detected between late stages of melanoma development and extra copies of the chromosome carrying the receptor gene (Koprowski et al., Somatic Cell and Molecular Genetics, Vol. 11, pp. 297–302, 1985).

Because of EGF-receptors are expressed on a wide variety of solid tumors they provide a suitable target for anti-tumor therapy. However, there is a need in the art for a suitable anti-receptor antibody. Many of the known antibodies have properties which would be deleterious if used as anti-tumor agents. For example, antibodies which mimic the effects of EGF could stimulate the progression of the tumor rather than arresting it. Other antibodies which only bind to high or low affinity receptors could be less than optimally effective because EGF could still exert its effect through the unbound receptors. Still other antibodies convert low affinity receptors to high affinity receptors, which could exacerbate tumor growth rather than inhibiting it. Thus there is a need in the art for an anti-EGF-receptor antibody which would be suitable for anti-tumor therapy.

Although murine MAbs have been used for therapeutic treatment in humans, they have elicited an immune response (Giorgi et al., 1983; Jaffers et al., 1986). To overcome this problem, several groups have tried to "humanize" murine antibodies. This can involve one of two approaches. Firstly, the murine constant region domains for both the light and heavy chain can be replaced with human constant regions. Such "chimeric" murine-human antibodies have been successfully constructed from several murine antibodies directed against human tumor-associated antigens (Sun et al., 1987; Whittle et al., 1987; Liu et al., 1987; Gillies and Wesolowski, 1990). This approach totally conserves the antigen-binding site of the murine antibody, and hence the antigen affinity, while conferring the human isotype and effector functions. In the second approach only the complementarity determining regions (CDRs) from the mouse variable regions are grafted together with human framework regions (FRs) of both the light and heavy chain variable domains ($V_L$ and $V_H$). It is reasoned that this technique will transfer the critical and major portion of the antigen-binding site to the human antibody (Jones et al., 1986).

CDR grafting has been carried out for several rodent monoclonals (Jones et al., 1986; Reichmann et al., 1988; Verhoeyen et al., 1988; Queen et al.; 1989; Co et al., 1991; Gorman et al., 1991; Maeda et al., 1991; Temptest et al., 1991). All retained their capacity to bind antigen, although the affinity was usually diminished. In most cases it was deemed necessary to alter certain amino acids in the human framework residues (FRs). Both chimeric and CDR grafted antibodies have proved superior to the mouse antibodies in the clinic (Hale et al., 1988; LoBuglio et al., 1989; Mathieson et al., 1990). However, a general teaching of which amino acids have to be changed, is not known and not completely predictable in any case.

EP 088 994 proposes the construction of recombinant DNA vectors comprising of a DNA sequence which codes for a variable domain of a light or a heavy chain of an immunoglobulin specific for a predetermined ligand. The application does not contemplate variations in the sequence of the variable domain.

EP 102 634 describes the cloning and expression in bacterial host organisms of genes coding for the whole or a part of human IgG heavy chain polypeptide, but does not contemplate variations in the sequence of the polypeptide.

EP 239 400 proposes that humanized antibodies can be obtained by replacing the antigen-binding site (hypervariable regions) of any human antibody by an antigen-binding site of a non-human, for example of a mouse or a rat antibody by genetechnological methods.

Thus, following this teaching, human or humanized antibodies can be manufactured having specific antigen-binding sites which were not available up to now in antibodies originating from humans.

Chimeric antibodies can be obtained by replacing not only the CDRs but the whole variable regions of the light and heavy chains. Chimeric antibodies, however, can still be immunogenic. Chimeric antibodies are, however, very useful for diagnostic purposes and optimizing humanized antibodies.

It could be shown that the affinity of the antigen-binding sites can be influenced by selective exchange of some single amino acids within the variable regions which are not directly part of the CDRs (Reichmann et al., 1988).

As consequence in the worst case, the binding affinity of the antigen can be completely lost if one works according to the teaching of the EP 239 400. This fact could be demonstrated by the inventors of the instant invention, who failed in constructing a correspondingly humanized antibody which was directed to epitopes of the EGF-receptor.

Therefore, it must be considered that the success of such a humanization depends on the constitution and conformation of the used variable regions and their interactions with the corresponding antigen-binding site. Thus, it is not completely predictable whether or which modifications within the variable domains of the antibody are necessary in order to obtain or to improve the binding of the antigen to the antibody.

SUMMARY OF THE INVENTION

Thus, the invention has the object of providing a humanized monoclonal antibody which is, in particular, directed to the EGF-receptor, comprising an antigen-binding site of non-human sources and the FRs of the variable regions and constant regions of human origins, which are, if necessary, modified in a way that the specificity of the binding site can be conserved or restored.

In particular, the invention has the object of characterizing the hypervariable regions of the antigen-binding site of an antibody against the EGF-receptor and providing these CDRs within a humanized monoclonal antibody defined as above.

This antibody and its chimeric variant can play an important role as a therapeutic or diagnostic agent in order to combat tumors, as melanoma, glioma or carcinoma.

It has been found, that effective and specific humanized monoclonal antibodies can be easily obtained by using a consensus sequence of at least the heavy chain variable regions of human immunoglobulins. In particular, all those consensus sequences are suitable which have a good (at least 60–70%, particularly 65–70%) identity compared with the variable regions of the original non-human antibodies.

Furthermore, it has been found, that these consensus sequences have to be modified only to a low extent whereas sometimes much more modifications have to be undertaken using variable regions of naturally occurring human antibodies. Often no or only a few modifications in the amino acid sequence are necessary according to the invention in order to receive a good specific antigen binding. Thus, only a few amino acids must be replaced in getting a perfect binding of the EGF-receptor to the preferred humanized antibody according to the invention, whereas no binding can be obtained here according to the teaching of the EP 239 400. The modifications which are necessary according to the invention can be indicated with 0 to 10%, or preferably, 1 to 5% related to the exchange of amino acids.

A humanized monoclonal antibody according to the invention has the following advantage: a consensus sequence which is a sequence according to the most common occurrence of amino acid on a distinct position of a chain of human immunoglobulin of a defined class or subclass or subgroup, can be synthesized as a whole or as a part without problems. There is no dependence on the detailed knowledge or availability of certain individual antibodies or antibody fragments. That means that a wide range of individually and naturally occurring antibody fragments can be covered by providing a very restricted number of consensus sequences which are cloned into corresponding expression vectors. A consensus sequence may be favorable with respect to the immunogenicity in comparison with individual natural sequences which are known to be sometimes epitopes for other antibodies (for example anti-idiotypic antibodies).

Although only one preferred embodiment was made, a general principal teaching is disclosed according to the instant invention. It is not a mere accident with respect to the large number of possible sequences and combinations of sequences in the variable and hypervariable domains that the described teaching regarding the consensus sequence succeeded in constructing a humanized antibody directed to the EGF-receptor.

Furthermore, it has been found, that the heavy chains of the variable domains provide a greater contribution to the antigen-binding site than the corresponding light chains. Therefore, it is not necessary to modify in the same manner the light chain of a humanized antibody having a consensus sequence. This is an interesting aspect because it is known that the light chains in some known natural antibodies play the more important role than the corresponding heavy chains (see Williams et al., 1990).

Finally and above all, the invention provides for the first time the characterization, cloning and amplification by means of genetic engineering the antigen-binding site of a murine antibody against the EGF-receptor (MAb 425). Corresponding oligonucleotides could be synthesized which code for that antigen-binding site and for the whole variable domain of a humanized and chimeric monoclonal antibody. The invention provides, moreover, correspondingly effective expression vectors which can be used for the transformation of suitable eukaryotic cells.

Thus, the invention relates to a humanized monoclonal antibody comprising antigen bindings sites (CDRs) of non-human origin, and the FRs of variable regions and constant regions of light and heavy chains of human origin, characterized in that at least the FRs of the variable regions of the heavy chain comprise a modified consensus sequence of different variable regions of a distinct class or subgroup of a human immunoglobulin.

In particular, the invention relates to a humanized monoclonal antibody, wherein the FRs of the consensus sequence has a homology of at least 70% compared with the amino acid sequence of the FRs of the variable region of the non-human antibody from which the antigen-binding sites originate.

In particular, the invention relates to a humanized monoclonal antibody, having the following properties:

(a) binds to human EGF-receptors;

(b) inhibits binding of EGF to EGF-receptor;

(c) inhibits the EGF-dependent tyrosine kinase activity of EGF-receptor;

(d) inhibits the growth of EGF-sensitive cells.

In particular, the invention relates to a humanized monoclonal antibody, wherein the hypervariable regions of the antigen-binding sites comprise the following amino acid sequences:

light chain

CDR-1 —Ser—Ala—Ser—Ser—Ser—Val—Thr—Tyr—Met—Tyr—(SEQ ID NO:2)
CDR-2 —Asp—Thr—Ser—Asn—Leu—Ala—Ser— (SEQ ID NO:2)
CDR-3 —Gln—Gln—Trp—Ser—Ser—His—Ile—Phe—Thr— (SEQ ID NO:3)

heavy chain

CDR-1 —Ser—His—Trp—Met—His—(SEQ ID NO:4)
CDR-2 —Glu—Phe—Asn—Pro—Ser—Asn—Gly—Arg—Thr—Asn—Tyr—Asn—Glu—Lys—Phe—Lys—Ser— (SEQ ID NO:5)
CDR-3 —Arg—Asp—Tyr—Asp—Tyr—Asp—Gly—Arg—Tyr—Phe—Asp—Tyr—(SEQ ID NO:6)

In particular, the invention relates to a humanized monoclonal antibody, wherein the FRs of the variable regions which are not related to the antigen-binding sites comprise the following amino acid sequence:

light chain

FR-1 —Asp—Ile—Gln—Met—Thr—Gln—Ser—Pro—Ser—Ser—Leu—Ser—Ala—Ser—Val—Gly—Asp—Arg—Val—Thr—Ile—Thr—Cys—(SEQ ID NO:7)
FR-2 —Trp—Tyr—Gln—Gln—Lys—Pro—Gly—Lys—Ala—Pro—Lys—Leu—Leu—Ile—Tyr—(SEQ ID NO:8)
FR-3 —Gly—Val—Pro—Ser—Arg—Phe—Ser—Gly—Ser—Gly—Ser—Gly—Thr—Asp—Tyr(Phe,Trp,His)—Thr—Phe—Thr—Ile—Ser—Ser—Leu—Gln—Pro—Glu—Asp—Ile—Ala—Thr—Tyr—Tyr—Cys—(SEQ ID NO:9)
FR-4 —Phe—Gly—Gln—Gly—Thr—Lys—Val—Glu—Ile—Lys—(SEQ ID NO:10 heavy chain

FR-1 —Gln—Val—Gln—Leu—Val—Gln—Ser—Gly—Ala—Glu—Val—Lys—Lys—Pro—Gly—Ala—Ser—Val—Lys—Val—Ser—Cys—Lys—Ala—Ser—Gly—Tyr—Thr—Phe—Thr(Ser)—(SEQ ID NO:11)
FR-2 —Trp—Val—Arg(His)—Gln—Ala(Lys,His)—Pro(Val)—Gly—Gln—Gly—Leu—Glu—Trp—Ile(Val,Leu)—Gly—(SEQ ID NO:12)
FR-3 —Lys(Arg,His)—Ala(Val,Pro—Gly)—Thr—Met—Thr—Val(Ala,Pro,Gly)—Asp—Thr—Ser—Thr—Asn—Thr—Ala—Tyr—Met—Glu(Asn)—Leu—Ser—Ser—Leu—Arg—Ser—Glu—Asp—Thr—Ala—Val—Tyr—Tyr—Cys—Ala—Ser—(SEQ ID NO:13)
FR-4 —Trp—Gly—Gln—Gly—Thr—Leu—Val—Thr—Val—Ser—Ser—(SEQ ID NO:14), and wherein the amino acids listed in the brackets are alternatives.

In particular, the invention relates to a humanized monoclonal antibody, wherein the constant regions of the heavy chain comprise the amino acid sequence of a gamma-1 chain, and the constant regions of the light chain comprise the amino acid sequence of a kappa chain of a human immunoglobulin.

In particular, the invention relates to a humanized monoclonal antibody, comprising a derivate of an amino acid sequence modified by amino acid deletion, substitution, addition or inversion within the variable and constant regions wherein the biological function of specific binding to the antigen is preserved.

Furthermore, the invention relates to an expression vector, suitable for transformation of host cells, characterized in that it comprises a DNA sequence coding for the variable and/or constant regions of the light and/or heavy chains of a humanized antibody.

Furthermore, the invention relates to humanized or chimeric monoclonal antibody, comprising hypervariable regions (CDRs) of antigen-binding sites of murine origin and the FRs of the variable regions of human or murine origin and constant regions of light and heavy chains of human origin, characterized in that the hypervariable regions comprise the following amino acid sequences, light chain CDR-1 —Ser—Ala—Ser—Ser—Ser—Val—Thr—Tyr—Met—Tyr—(SEQ ID NO:2)
CDR-2 —Asp—Thr—Ser—Asn—Leu—Ala—Ser— (SEQ ID NO:2)
CDR-3 —Gln—Gln—Trp—Ser—Ser—His—Ile—Phe—Thr— (SEQ ID NO:3)

heavy chain

CDR-1 —Ser—His—Trp—Met—His—(SEQ ID NO:4)
CDR-2 —Glu—Phe—Asn—Pro—Ser—Asn—Gly—Arg—Thr—Asn—Tyr—Asn—Glu—Lys—Phe—Lys—Ser— (SEQ ID NO:5)
CDR-3 —Arg—Asp—Tyr—Asp—Tyr—Asp—Gly—Arg—Tyr—Phe—Asp—Tyr—(SEQ ID NO:6, and wherein the constant regions of the heavy chain comprise the amino acid sequence of a gamma-1 chain, and the constant regions of the light chain comprise the amino acid sequence of a kappa chain of a human immunoglobulin.

In particular, the invention relates to a humanized monoclonal antibody according to claim 12, wherein the FRs of the variable regions which are not related to the antigen-binding sites, are of human origin and comprise the following amino acid sequence, light chain FR-1 —Asp—Ile—Gln—Met—Thr—Gln—Ser—Pro—Ser—
Ser—Leu—Ser—Ala—Ser—Val—Gly—Asp—Arg—Val—
Thr—Ile—Thr—Cys—(SEQ ID NO:7)
FR-2 —Trp—Tyr—Gln—Gln—Lys—Pro—Gly—Lys—Ala—
Pro—Lys—Leu—Leu—Ile—Tyr—(SEQ ID NO:8)
FR-3 Gly—Val—Pro—Ser—Arg—Phe—Ser—Gly—Ser—Gly—
Ser—Gly—Thr—Asp—Tyr(Phe,Trp,His)—Thr—Phe—
Thr—Ile—Ser—Ser—Leu—Gln—Pro—Glu—Asp—Ile—
Ala—Thr—Tyr—Tyr—Cys—(SEQ ID NO:9)
FR-4 —Phe—Gly—Gln—Gly—Thr—Lys—Val—Glu—Ile—
Lys—(SEQ ID NO:10)

heavy chain

FR-1 —Gln—Val—Gln—Leu—Val—Gln—Ser—Gly—Ala—
Glu—Val—Lys—Lys—Pro—Gly—Ala—Ser—Val—Lys—
Val—Ser—Cys—Lys—Ala—Ser—Gly—Tyr—Thr—Phe—
Thr(Ser)—(SEQ ID NO:11)
FR-2 —Trp—Val—Arg(His)—Gln—Ala(Lys,His)—Pro(Val)—
Gly—Gln—Gly—Leu—Glu—Trp—Ile(Val,Leu)—Gly—
(SEQ ID NO:12)
FR-3 —Lys(Arg,His)—Ala(Val,Pro,Gly)—Thr—Met—Thr—
Val(Ala,Pro,Gly)—Asp—Thr—Ser—Thr—Asn—Thr—
Ala—Tyr—Met—Glu(Asn)—Leu—Ser—Ser—Leu—Arg—
Ser—Glu—Asp—Thr—Ala—Val—Tyr—Tyr—Cys—Ala—
Ser—(SEQ ID NO:13)
FR-4 —Trp—Gly—Gln—Gly—Thr—Leu—Val—Thr—Val—
Ser—Ser—(SEQ ID NO:16)

In particular, the invention relates to a chimeric monoclonal antibody according to claim 12, wherein the FRs of the variable regions which are not related to the antigen-binding site, are of murine origin and comprise the following amino acid sequences:

light chain

FR-1 —Gln—Ile—Val—Leu—Thr—Gln—Ser—Pro—Ala—Ile—
Met—Ser—Ala—Ser—Pro—Gly—Glu—Lys—Val—Thr—
Met—Thr—Cys—(SEQ ID NO:15)
FR-2 —Trp—Tyr—Gln—Gln—Lys—Pro—Gly—Ser—Ser—
Pro—Arg—Leu—Leu—Ile—Tyr—(SEQ ID NO:16)
FR-3 —Gly—Val—Pro—Val—Arg—Phe—Ser—Gly—Ser—
Gly—Ser—Gly—Thr—Ser—Tyr—Ser—Leu—Thr—Ile—
Ser—Arg—Met—Glu—Ala—Glu—Asp—Ala—Ala—Thr—
Tyr—Tyr—Cys—(SEQ ID NO:17
FR-4 —Phe—Gly—Ser—Gly—Thr—Lys—Leu—Glu—Ile—
Lys—(SEQ ID NO:18)

heavy chain

FR-1 —Gln—Val—Gln—Leu—Gln—Gln—Pro—Gly—Ala—
Glu—Leu—Val—Lys—Pro—Gly—Ala—Ser—Val—Lys—
Leu—Ser—Cys—Lys—Ala—Ser—Gly—Tyr—Thr—Phe—
Thr—(SEQ ID NO:19)
FR-2 —Trp—Val—Lys—Gln—Arg—Ala—Gly—Gln—Gly—
Leu—Glu—Trp—Ile—Gly—(SEQ ID NO:20)
FR-3 —Lys—Ala—Thr—Leu—Thr—Val—Asp—Lys—Ser—
Ser—Ser—Thr—Ala—Tyr—Met—Gln—Leu—Ser—Ser—
Leu—Thr—Ser—Glu—Asp—Ser—Ala—Val—Tyr—Tyr—
Cys—Ala—Ser—(SEQ ID NO:21)
FR-4 —Trp—Gly—Gln—Gly—Thr—Thr—Leu—Thr—Val—
Ser—Ser—(SEQ ID NO:22)

Moreover, the invention relates to an expression vector, suitable for transformation of host cells, characterized in that it comprises DNA sequences coding for the variable and/or constant regions of the light and/or heavy chains of a humanized or chimeric monoclonal antibody.

Furthermore, the invention relates to a process for the preparation of a humanized monoclonal antibody, comprising hypervariable regions (CDRs) of antigen-binding sites of non-human origin, and FRs of variable regions and constant regions of the light and heavy chains of human origin by cultivating transformed host cells in a culture medium and purification and isolation the expressed antibody proteins, characterized in (a) synthesizing or partially synthesizing or isolating an oligonucleotide sequence which codes for an amino acid consensus sequence of different variable regions (FR-1 to FR-4) of a heavy chain of a class or a subgroup of a human immunoglobulin, wherein the used consensus sequence has a homology of at least 70% compared with the amino acid sequence of the FRs of the variable regions of the non-human antibody from which the antigen-binding sites originate, and wherein the consensus sequence is modified by alterations of maximum 10% of the amino acids in order to preserve the binding capability of the antigen to the hypervariable regions;

(b) synthesizing or partially synthesizing or isolating an oligonucleotide sequence which codes for an amino acid consensus sequence under the conditions given in (a) of different variable regions (FR-1 to FR-4) of a light chain of a class or a subgroup of a human immunoglobulin, or, alternatively, which codes for a corresponding natural occurring amino acid sequence;

(c) in each case synthesizing or partially synthesizing or isolating an oligonucleotide sequence which codes for the amino acid sequence of the hypervariable regions (CDRs) of the light and heavy chain corresponding to the hypervariable regions of the basic non-human antibody;

(d) in each case synthesizing or partially synthesizing or isolating an oligonucleotide sequence which codes for the amino acid sequence of the constant regions of the light and heavy chain of a human immunoglobulin;

(e) constructing one or several expression vectors comprising in each case at least a promoter, a replication origin and the coding DNA sequences according to (a) to (d), wherein the DNA sequences coding for the light and heavy chains can be present together in one or, alternatively, in two or more different vectors,
and finally, (f) transforming the host cells with one or more of the expression vectors according to (e).

In particular, the invention relates to a process, wherein DNA sequences are used coding for the following amino acid sequences which represent the hypervariable regions (CDRs):

light chain

CDR-1 —Ser—Ala—Ser—Ser—Ser—Val—Thr—Tyr—Met—
Tyr—(SEQ ID NO:1)
CDR-2 —Asp—Thr—Ser—Asn—Leu—Ala—Ser—
(SEQ ID NO:2)
CDR-3 —Gln—Gln—Trp—Ser—Ser—His—Ile—Phe—Thr—
(SEQ ID NO:3)

heavy chain

CDR-1 —Ser—His—Trp—Met—His—(SEQ ID NO:4)
CDR-2 —Glu—Phe—Asn—Pro—Ser—Asn—Gly—Arg—Thr—
Asn—Tyr—Asn—Glu—Lys—Phe—Lys—Ser—
(SEQ ID NO:5)
CDR-3 —Arg—Asp—Tyr—Asp—Tyr—Asp—Gly—Arg—Tyr—
Phe—Asp—Tyr—(SEQ ID NO:6)

In particular, the invention relates to a process, wherein DNA sequences are used coding for the following amino acid sequences which represent the FRs of the variable regions:

light chain

FR-1 —Asp—Ile—Gln—Met—Thr—Gln—Ser—Pro—Ser—
Ser—Leu—Ser—Ala—Ser—Val—Gly—Asp—Arg—
Val—Thr—Ile—Thr—Cys—(SEQ ID NO:7)
FR-2 —Trp—Tyr—Gln—Gln—Lys—Pro—Gly—Lys—Ala—

-continued

| | |
|---|---|
| | Pro—Lys—Leu—Leu—Ile—Tyr—(SEQ ID NO:8) |
| FR-3 | —Gly—Val—Pro—Ser—Arg—Phe—Ser—Gly—Ser—Gly—Ser—Gly—Thr—Asp—Tyr(Phe,Trp,His)—Thr—Phe—Thr—Ile—Ser—Ser—Leu—Gln—Pro—Glu—Asp—Ile—Ala—Thr—Tyr—Tyr—Cys—(SEQ ID NO:9) |
| FR-4 | —Phe—Gly—Gln—Gly—Thr—Lys—Val—Glu—Ile—Lys—(SEQ ID NO:10) | heavy chain

| | |
|---|---|
| FR-1 | —Gln—Val—Gln—Leu—Val—Gln—Ser—Gly—Ala—Glu—Val—Lys—Lys—Pro—Gly—Ala—Ser—Val—Lys—Val—Ser—Cys—Lys—Ala—Ser—Gly—Tyr—Thr—Phe—Thr(Ser)—(SEQ ID NO:11) |
| FR-2 | —Trp—Val—Arg(His)—Gln—Ala(Lys,His)—Pro(Val)—Gly—Gln—Gly—Leu—Glu—Trp—Ile(Val,Leu)—Gly—(SEQ ID NO:12) |
| FR-3 | —Lys(Arg,His)—Ala(Val,Pro,Gly)—Thr—Met—Thr—Val(Ala,Pro,Gly)—Asp—Thr—Ser—Thr—Asn—Thr—Ala—Tyr—Met—Glu(Asn)—Leu—Ser—Ser—Leu—Arg—Ser—Glu—Asp—Thr—Ala—Val—Tyr—Tyr—Cys—Ala—Ser—(SEQ ID NO:13) |
| FR-4 | —Trp—Gly—Gln—Gly—Thr—Leu—Val—Thr—Val—Ser—Ser(SEQ ID NO:14) |

Moreover, the invention relates to a process for the preparation of a chimeric monoclonal antibody having the biological function of binding to epitopes of the EGF-receptor, comprising hypervariable regions (CDRs) of antigen-binding sites and FRs of variable regions of murine origin and FRs of variable regions of murine origin and constant regions of the light and heavy chains of human origin by cultivating transformed host cells in a culture medium and purification and isolation the expressed antibody proteins, characterized in that the host cells are transformed with expression vectors according to one of the expression vectors.

Furthermore, the invention relates to a pharmaceutical composition comprising a humanized or chimeric monoclonal antibody.

Furthermore, the invention relates to the use of humanized or chimeric antibody for the manufacture of a medicament directed to tumors.

Finally, the invention relates to the use of humanized or chimeric antibody for diagnostic locating and assessing tumor growth.

To sum up, the invention relates to a monoclonal antibody comprising a consensus sequence of variable regions of a heavy chain of a class or a subgroup of human immunoglobulins.

The entire disclosures of all applications, patents and publications, if any, cited above and below, and of corresponding European Patent application 91 103 389.2, filed Mar. 6, 1991, are hereby incorporated by reference.

Microorganisms and plasmids used in the invention:

(a) pRVL425 (=HCMV-RV$_L$b425-k), deposited on Feb. 1, 1991, according to the Budapest Treaty at the Deutsche Sammlung von Mikroorganismen (DSM) under the accession No. DMS 6340. The expression vector contains the sequences of the hypervariable regions (CDRs) of the murine antibody 425 and the FRs of the variable region and the constant (kappa) region of the light chain of the humanized antibody. R is standing for "reshaped".

(b) pRVH425 (=HCMV-RV$_H$g425-γ), deposited on Feb. 1, 1991, according to the Budapest Treaty at the Deutsche Sammlung yon Mikroorganismen (DSM) under the accession No. DSM 6339. The expression vector contains the sequences of the hypervariable regions (CDRs) of the murine antibody 425 and the FRs of variable region and constant (gamma-1) region of the heavy chain of the humanized antibody. R is standing for "reshaped".

(c) pCVL425 (=HCMV-CV$_L$425-k), deposited on Feb. 1, 1991, according to the Budapest Treaty at the Deutsche Sammlung von Mikroorganismen (DSM) under the accession No. DSM 6338. The expression vector contains the sequences of the FRs and hypervariable regions (CDRs) of the light chain variable region of the murine antibody 425 and the constant (kappa) region of the light chain of human immunoglobulin. C is standing for chimeric.

(d) pCVH425 (=HCMV-CV$_H$425-γ), deposited on Feb. 1, 1991, according to the Budapest Treaty at the Deutsche Sammlung von Mikroorganismen (DSM) under the accession No. DSM 6337. The expression vector contains the sequences of the FRs and hypervariable regions (CDRs) of the light chain variable region of the murine antibody 425 and the constant region of the light chain of the human gamma-1 immunoglobulin. C is standing for chimeric.

(e) Hybridma cell line 425, deposited on Jan. 26, 1988, according to Budapest Treaty at the American Type Culture Collection (ATCC) under the accession No. HB 9629. The cell line produces the murine antibody 425 which is directed to the EGF-receptor.

Other biological materials:

Other microorganisms, cell lines, plasmids, promoters, resistance markers, replication origins or other fragments of vectors which are mentioned in the application are commercially or otherwise generally available. Provided that no other hints in the application are given, they are used only as examples and are not essential according to the invention and can be replaced by other suitable tools and biological materials, respectively.

Bacterial hosts are preferably used for the amplification of the corresponding DNA sequences. Examples for these host are: *E. coli* or Bacillus.

Eukaryotic cells like COS (CV1 origin SV40) or CHO (Chinese hamster ovary) cells or yeasts, for example, are preferred in order to produce the humanized and chimeric antibodies according to the invention. COS and CHO cells are preferred.

General methods for manufacturing:

The techniques which are essential according to the invention are described in detail in the specification.

Other techniques which are not described in detail correspond to known standard methods which are well known to a person skilled in the art or are described more in detail in the cited references and patent applications and in standard literature.

BRIEF DESCRIPTION OF THE FIGURES

FIG. 1 Schematic representations of the vectors used for the expression of chimeric and reshaped human antibodies. Restriction sites used in the construction of the expression plasmids are marked. The variable region coding sequences are represented by the dark boxes, constant regions by the light boxes, the HCMV promoter and enhancer by the hatched boxes, and the nucleotide fragment from the plasmid pSVneo by the speckled boxes. The directions of transcription are represented by arrows.

FIG. 2 The nucleotide and amino acid sequences of the V$_H$425 (A) (SEQ ID NO:23 and SEQ ID NO:24), and V$_L$425 (B) SEQ ID NO:25 and SEQ ID NO:26), cDNA as cloned into pUC18. The amino acids contributing to the leader are underlined and CDRs are indicated by brackets. The splice sites between the variable regions and constant regions are also shown. The front and back PCR-primers and their annealing sites, used in the construction of the genes coding for the chimeric antibodies, are shown.

FIG. 3 The nucleotide (SEQ ID NO:27) and amino acid (SEQ ID NO:28) sequences of the synthesized gene fragment coding for reshaped human $V_H$a425. The leader sequence is underlined and residues contributing to the CDRs are bracketed.

FIG. 4 Comparison of the amino acid sequences of mouse and reshaped human 425 variable regions. FIG. 4A shows the sequences of mouse $V_L$ ($V_L$425) and reshaped human $V_L$S (RV$_L$a425 and RV$_L$b425). FIG. 4B shows the sequences of mouse $V_H$ ($V_H$425) and reshaped human $V_H$S (RV$_H$a425, RV$_H$b425, RV$_H$c425, RV$_H$d425, RV$_H$e425, RV$_H$f425, RV$_H$g425, RV$_H$h425, and RV$_H$i425). The FRs and CDRs are indicated. Amino acids are numbered according to Kabat et al., 1987.

Figure 7A:
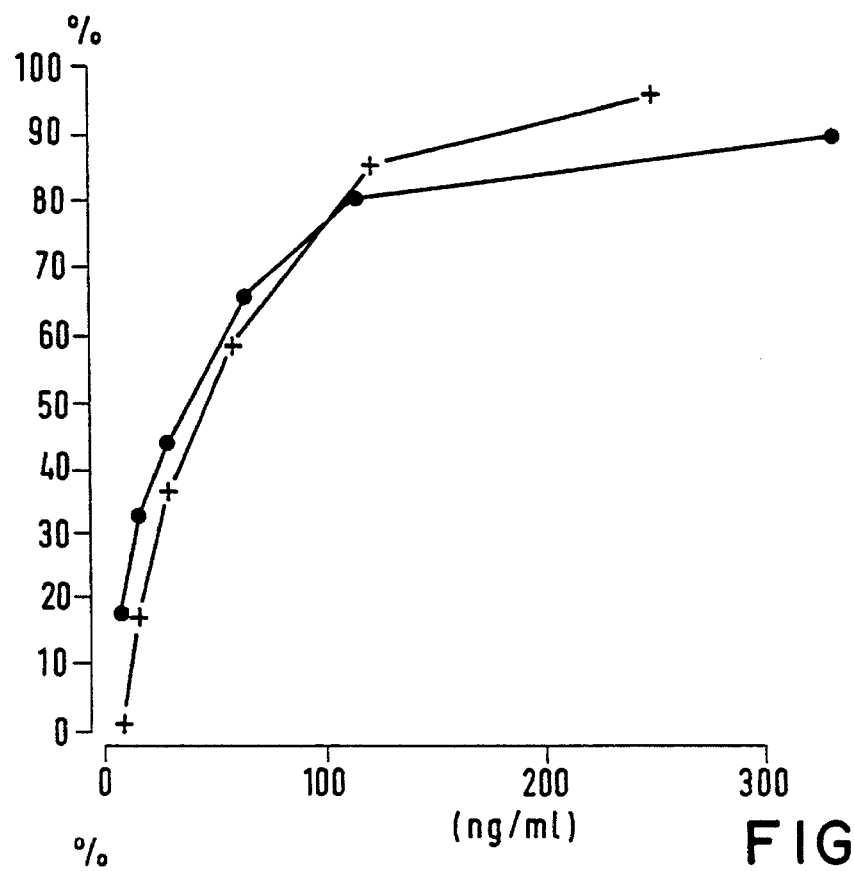
Figure 7B:
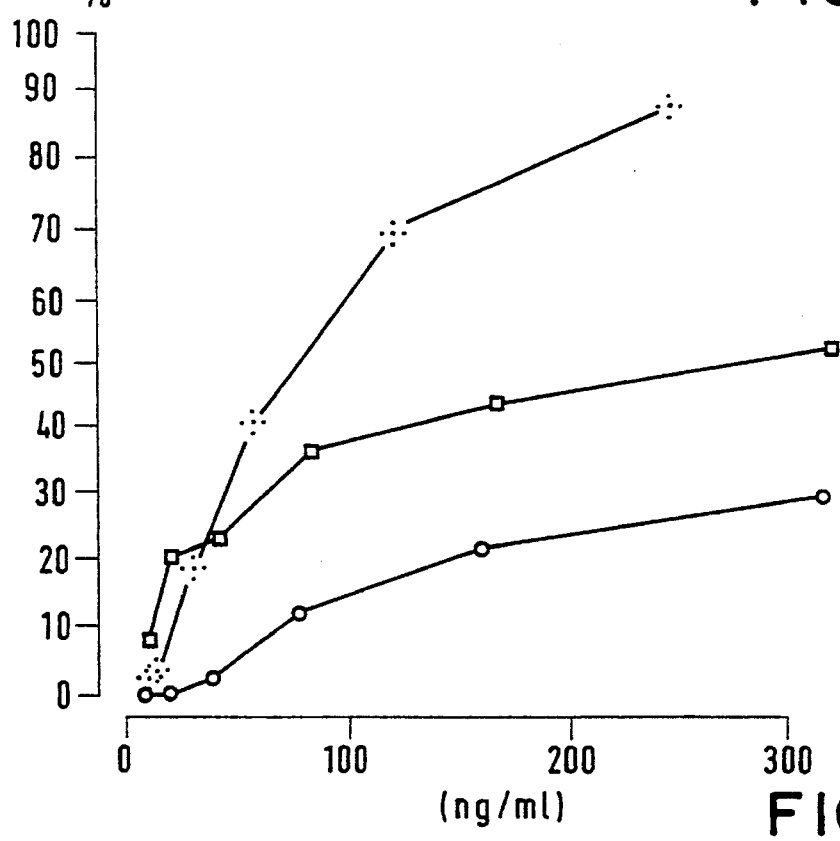

The sequences in the figure have the following Sequence Identifiers:

FIG. 7 Competition for binding to antigen. Panel A shows competition between labelled mouse 425 antibody and (1) unlabelled mouse 425 antibody (+) and (2) chimeric 425 antibody (●) produced by COS cells after co-transfection with HCMV-CV$_L$425-kappa and HCMV-C$_H$425 -gamma-1. Panel B shows competition between labelled mouse 425 antibody and (1) unlabelled mouse 425 antibody (+) and (2) the reshaped human 425 antibodies produced by COS cells after co-transfection with HCMV-RV$_L$a425-kappa and HCMV-RV$_H$i425-gamma-1 (o), and with HCMV-RV$_L$a425-kappa and HCMV-RV$_H$g425-gamma-1 (¤). In each case, the horizontal axis represents the concentration of inhibitor (ng/ml). The vertical axis represents percentage of inhibition of binding.

Figure 8A:
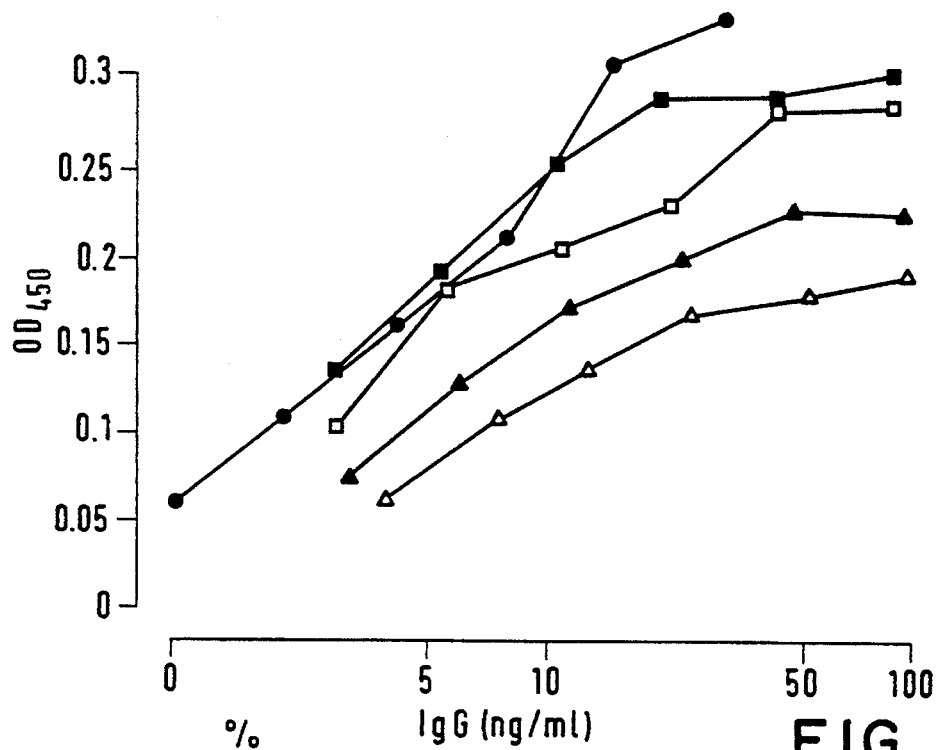
Figure 8B:
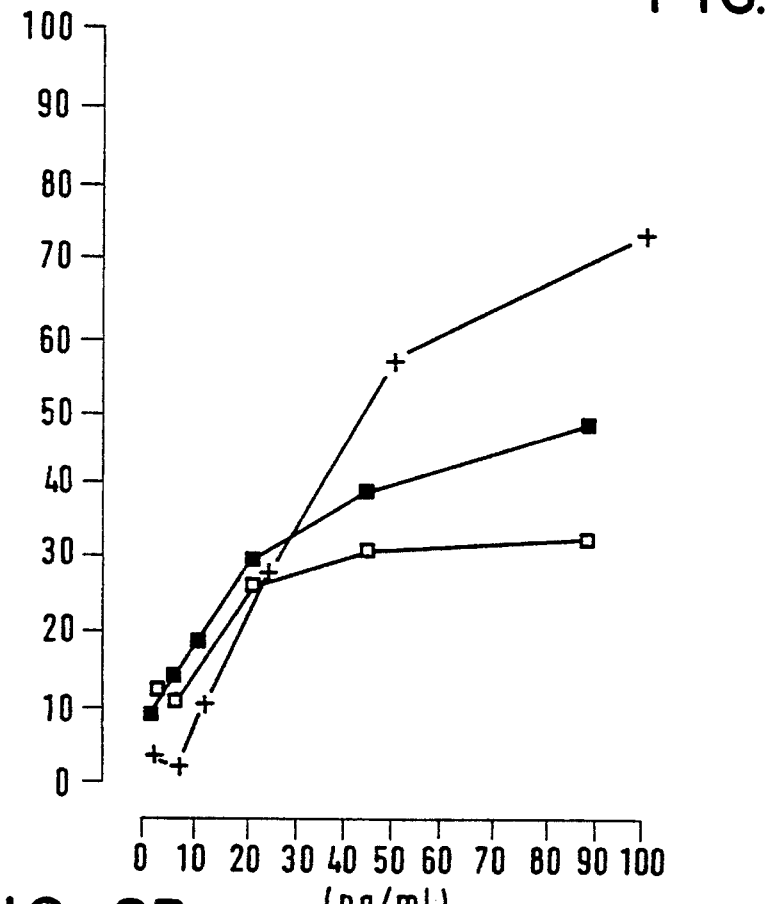

FIG. 8 An examination of the effects of different reshaped human $V_L$ regions on antigen-binding. Panel A shows antigen-binding by reshaped human antibodies produced in COS cells transfected with HCMV-CV$_L$425-kappa and HCMV-CV$_H$425-gamma-1 (●), HCMV-RV$_L$a425-kappa and HCMV-RV$_H$ g425-gamma-1 (¤), HCMV-RV$_L$b425-

| | Panel A | | |
|---|---|---|---|
| | $V_L$425 | RV$_L$a425 | RV$_L$b425 |
| FR-1 | 15 | 7 | 7 |
| CDR-1 | 1 | 1 | 1 |
| FR-2 | 16 | 8 | 8 |
| CDR-2 | 2 | 2 | 2 |
| FR-3 | 17 | 9[a] | 9[b] |
| CDR-3 | 3 | 3 | 3 |
| FR-4 | 18 | 10 | 10 |

[a] $Xaa_{15}$ = Phe
[b] $Xaa_{15}$ = Tyr

| | Panel B | | | | | | | | |
|---|---|---|---|---|---|---|---|---|---|
| | $V_H$425 | RV$_H$a | RV$_H$b | RV$_H$c | RV$_H$d | RV$_H$e | RV$_H$f | RV$_H$g | RV$_H$h | RV$_H$i |
| FR-1 | 19 | 11[c] | 11[c] | 11[c] | 11[c] | 11[d] | 11[c] | 11[d] | 11[d] | 11[d] |
| CDR-1 | 4 | 4 | 4 | 4 | 4 | 4 | 4 | 4 | 4 | 4 |
| FR-2 | 20 | 12[e] | 12[e] | 12[e] | 12[f] | 12[f] | 12[f] | 12[f] | 12[e] | 12[e] |
| CDR-2 | 5 | 5 | 5 | 5 | 5 | 5 | 5 | 5 | 5 | 5 |
| FR-3 | 21 | 13[g,i] | 13[g,j] | 13[h,j] | 13[g,i] | 13[g,i] | 13[h,j] | 13[h,j] | 13[g,j] | 13[h,j] |
| CDR-3 | 6 | 6 | 6 | 6 | 6 | 6 | 6 | 6 | 6 | 6 |
| FR-4 | 22 | 14 | 14 | 14 | 14 | 14 | 14 | 14 | 14 | 14 |

[a] $Xaa_{15}$ = Phe
[b] $Xaa_{15}$ = Tyr
[c] $Xaa_{30}$ = Ser
[d] $Xaa_{30}$ = Thr
[e] $Xaa_{13}$ = Val
[f] $Xaa_{13}$ = Ile
[g] $Xaa_1$ = Arg, $Xaa_2$ = Val, $Xaa_{16}$ = Glu
[h] $Xaa_1$ = Lys, $Xaa_2$ = Ala, $Xaa_{16}$ = Glu
[i] $Xaa_6$ = Leu
[j] $Xaa_6$ = Val

Figure 1A:
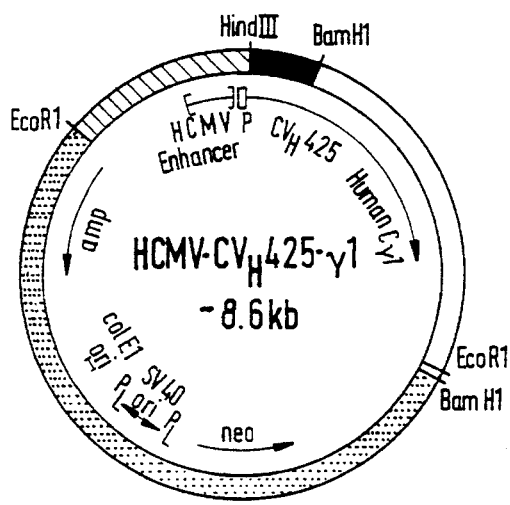
FIG. 1A=plasmid HCMV-CV$_H$425-γ1.
Figure 1B:
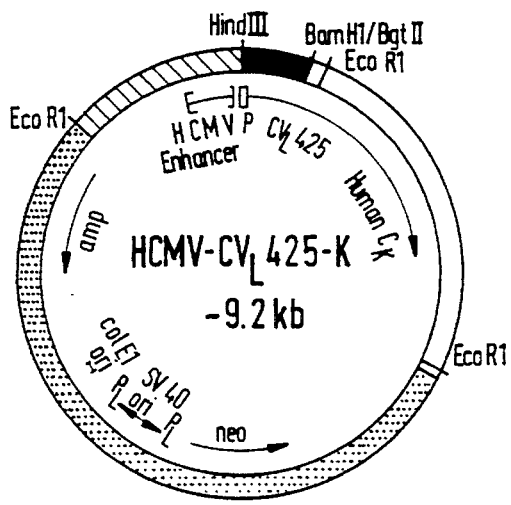
FIG. 1B=plasmid HCMV-CV$_L$425-K.
Figure 1C:
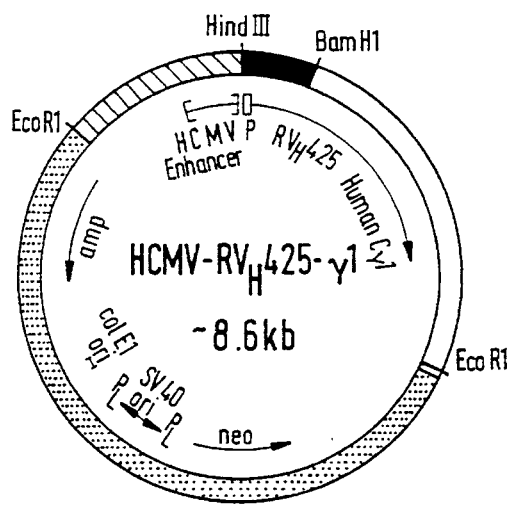
FIG. 1C=plasmid HCMV-RV$_H$425-γ1.
Figure 1D:
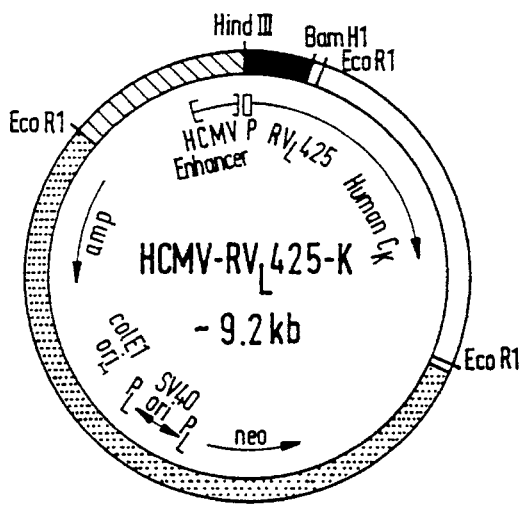
FIG. 1D=plasmid HCMV-RV$_L$425-K.
Figure 5:
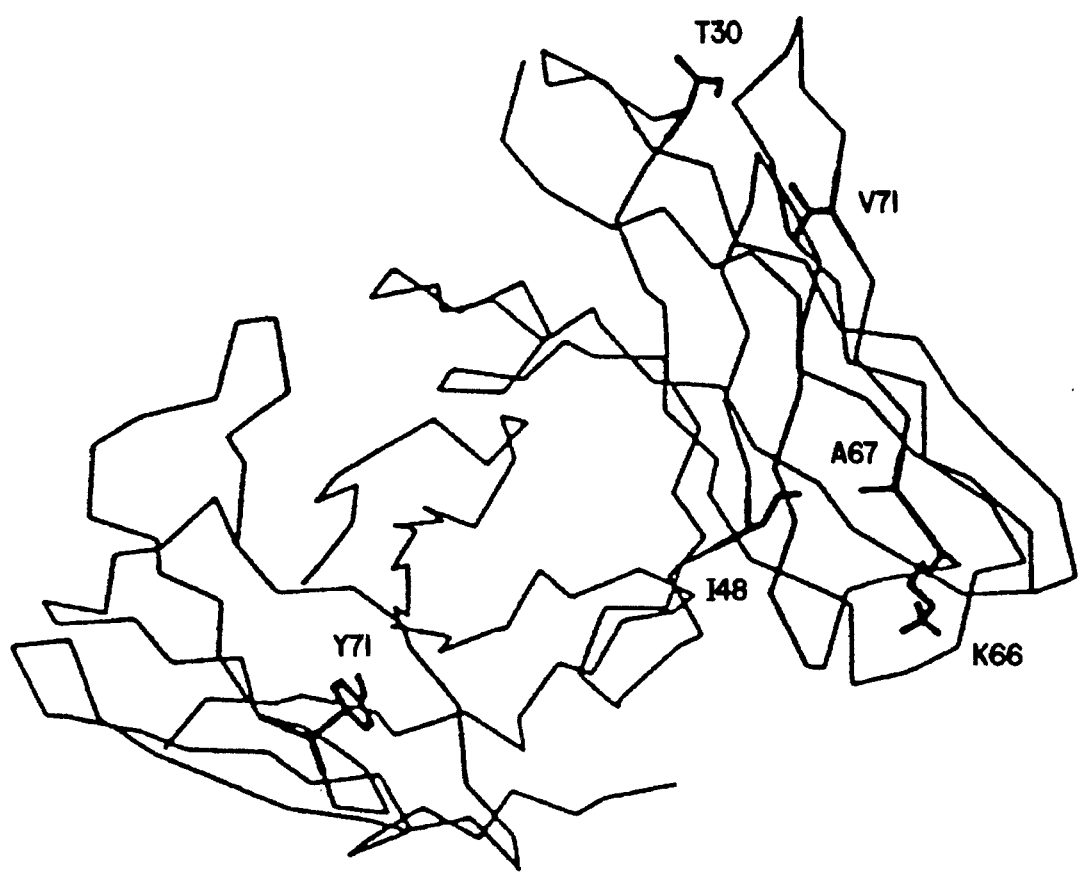

FIG. 5 Molecular model of the mouse MAb 425 variable regions showing the location of particular amino acid residues in the backbone.

Figure 6:
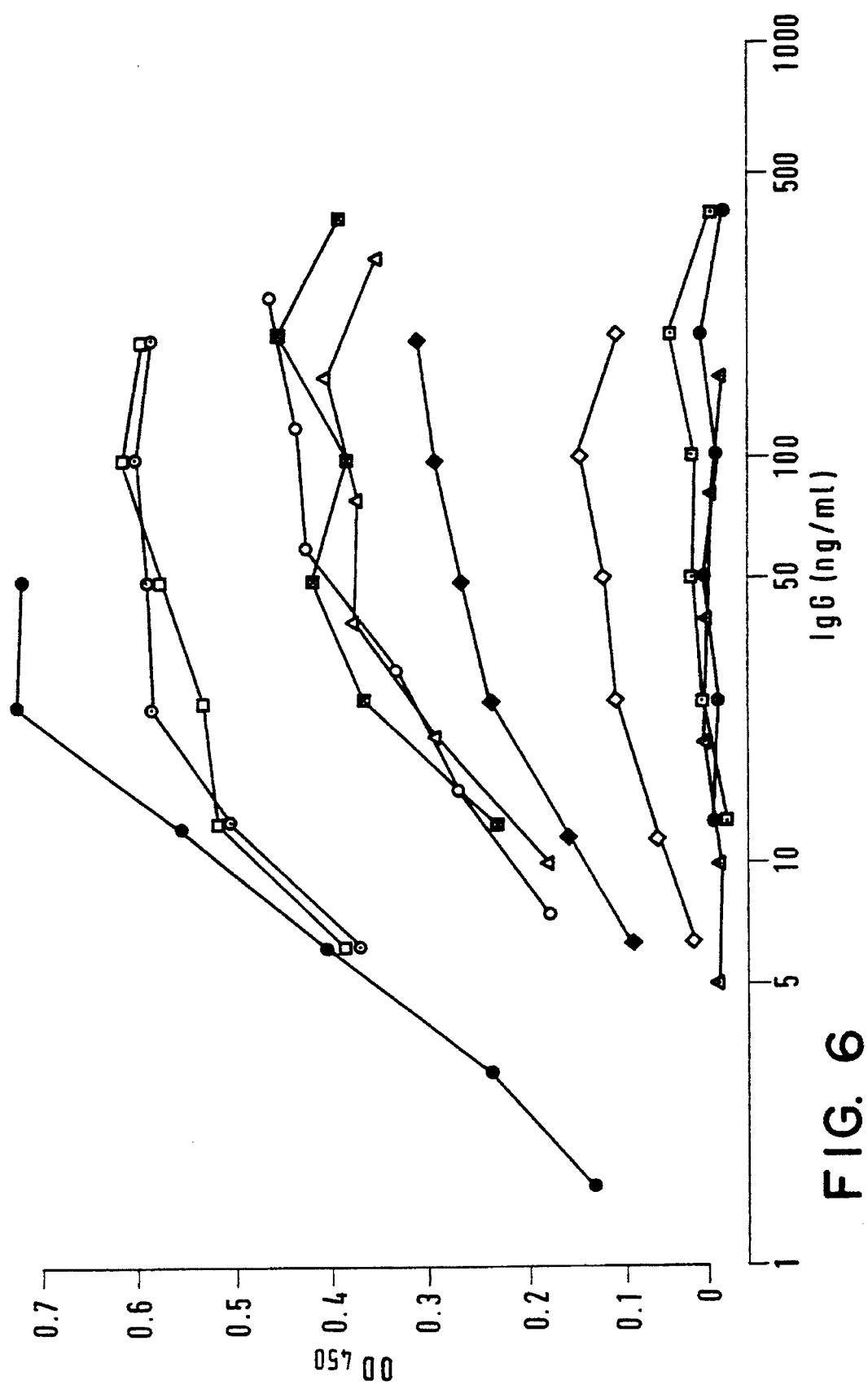

FIG. 6 Detection of binding to EGFR by ELISA. Antigen-binding activity was assayed in dilutions of transfected COS cell supernatants and plotted as optical density at 450 nm against concentration of IgG (quantitated by ELISA, see Materials and Methods). All versions of reshaped human $V_H$ regions were cotransfected with RV$_L$a425 and are represented as follows: RV$_H$a425 △, RV$_H$b425 ◇, RV$_H$c425 ▲, RV$_H$d425 ⊗, RV$_H$e425 □, RV$_H$f425 ▨, RF$_H$g425 □, RV$_H$h425 o, RV$_H$i425 ⊙, RV$_H$b425 co-transfected with RV$_L$b425 is represented as ♦. A co-transfection of the chimeric VL425 and VH425 are represented as ●.

kappa and HCMV-RV$_H$ g425-gamma-1 (■) , HCMV-RV$_L$a425-kappa and HCMV-RV$_H$ c425-gamma-1 (△), and HCMV-RV$_L$b425-kappa and HCMV-RV$_H$ c425-gamma-1 (▲). Panel B shows competition for binding to antigen between labelled mouse 425 antibody and (1) unlabelled mouse 425 antibody (+) and (2) reshaped human 425 antibodies produced in COS cells co-transfected with HCMV-V$_L$a425-kappa and HCMV-V$_H$ g425-gamma-1 (¤) and with HCMV-V$_L$b425-kappa and HCMV-V$_H$g425-gamma-1 (■). In panel A, the vertical axis represents the optical density at 450 nm (OD$_{450}$) and the horizontal axis represents the concentration of IgG (ng/ml). In panel B, the horizontal axis represents the concentration of inhibitor (ng/ml) and the vertical axis represents percentage of inhibition of binding.

Figure 9:
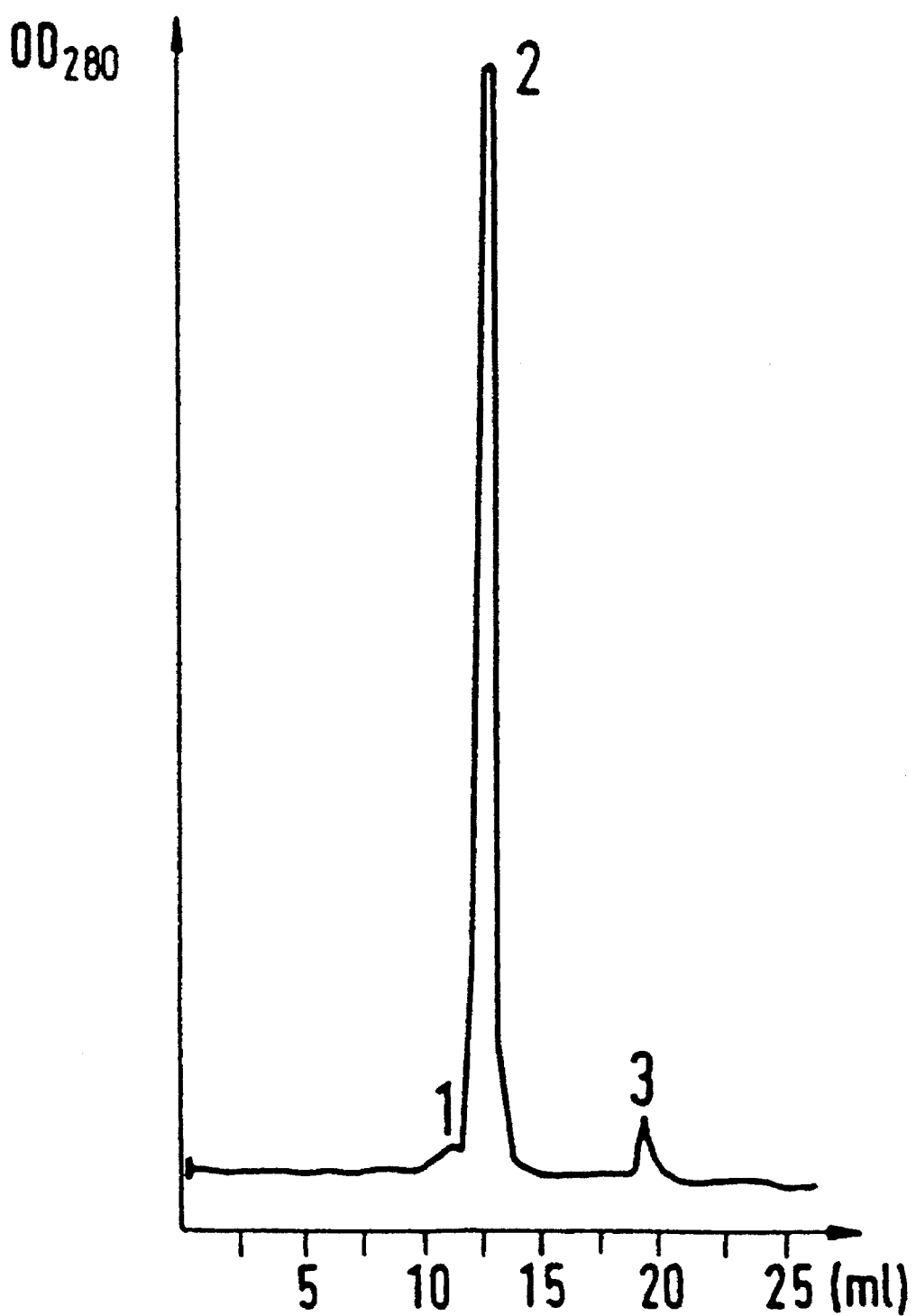

FIG. 9 Purification by gel filtration of reshaped MAb 425 on SUPEROSE 12™. Peak 2 represents IgG.

Figure 10:
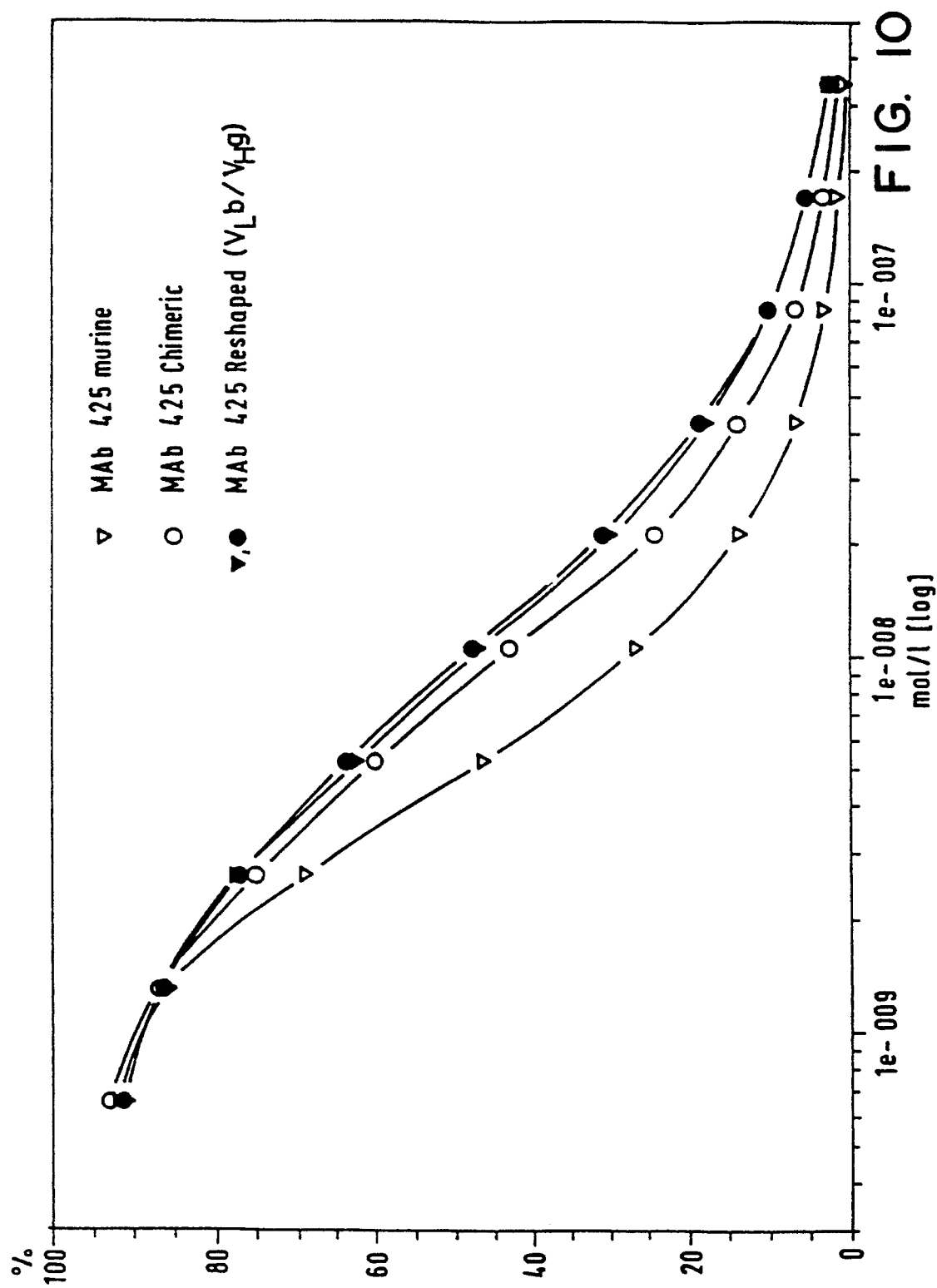

FIG. 10 Competitive binding of murine, chimeric and reshaped MAbs 425 to EGF-receptor (EGFR). The vertical axis represents the ratio bound (MAb) to total (MAID) in % (% bound/total). The horizontal axis represents the concentration of antibody (mol/l [log]).

▽ means MAb 425 murine o means MAb 425 chimeric

●, ▼ mean MAb 425 reshaped ($V_L b/V_{Hg}$)

Figure 11:
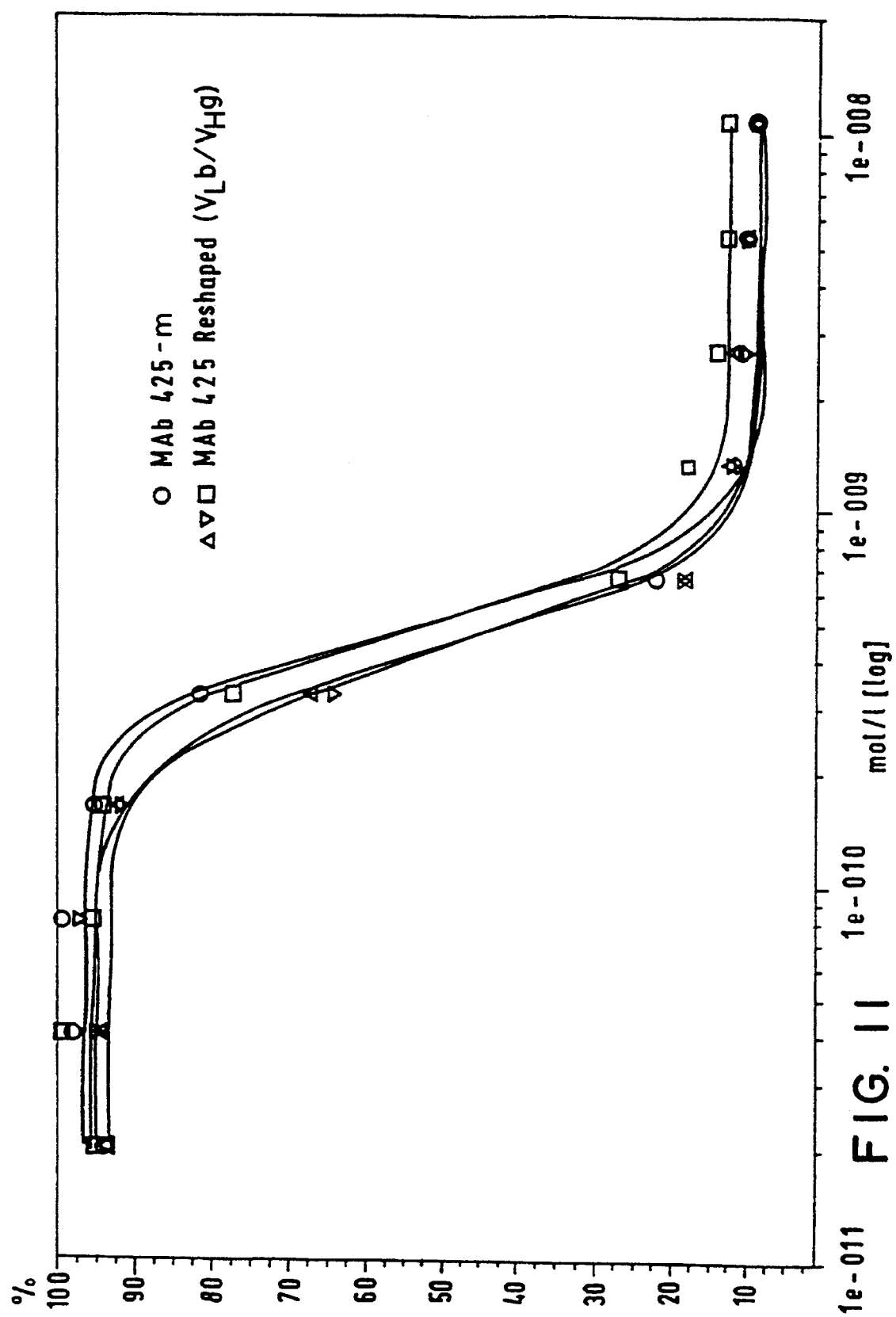

FIG. 11 Competition of EGF and antibodies to EGF-receptor. The vertical axis represents % bound/total (MAb). The horizontal axis represents the concentration of antibody (mol/l [log]).

o means MAb 425 murine

△, ▽, ¤ mean MAb 425 reshaped ($V_L b/V_{Hg}$)

DETAILED DESCRIPTION

Cloning and sequencing of variable region genes of MAb 425:

From the cDNA synthesis and cloning using the kappa chain primer, 300–400 colonies are preferably picked for screening. From the cDNA synthesis and cloning using the gamma-2a primer, 200–300 colonies are preferably for screening. After screening by hybridization using the two respective cloning primers, 20–30 light chain colonies and 10–20 heavy chain colonies give strong signals. Plasmid DNA is isolated from these colonies and analyzed by usual and commercially available restriction enzyme digests to determine the size of the cDNA inserts. Clones that appear to have inserts 400–500 bp or 500–600 bp for $V_L$ and $V_H$ cloning, respectively, are selected as candidates for sequencing. Three $V_L$ clones and three $V_H$ clones are sequenced on both strands using M13 universal and reverse sequencing primers. Of the three possible $V_L$ clones sequenced, one codes for a complete variable region and the others appeal to code for unrelated peptides. Two of the $V_H$ clones code for identical $V_H$ regions while the other appears to code for the $V_H$ region with the intron between the leader sequence and FR-1 still present. Apart from the intron, the third $V_H$ clone contains coding sequence identical to that of the first two clones. To verify the sequence of the $V_L$ region, three more cDNA clones containing inserts of the appropriate size are sequenced. Two of these give sequences in agreement with the first $V_L$ clone. The third is an unrelated DNA sequence. In the clones sequenced, not all of the original primer sequence are present. The extent of the deletions varies from clone to clone. These deletions, which probably occur during cDNA synthesis and cloning, may decrease the efficiency of the colony screening.

The $V_L$ and $V_H$ genes for MAb 425 are shown in FIG. 2. The amino acid sequence of the 425 $V_L$ and $V_H$ regions, are compared to other mouse variable regions in the Kabat data base (Kabat et al., 1987). The $V_L$ region can be classified into the mouse kappa chain variable region subgroup IV or VI. Within the FRs, the 425 $V_L$ region has an approximately 86% identity to the consensus sequence for mouse kappa subgroup IV and an approximately 89% identity to subgroup VI. The 425 $V_L$ region appear to use the JK4 segment. Examination of the VH region shows an approximately 98% identity to the FRs of the consensus sequence for mouse heavy chain subgroup II (B).

The choice of a suitable human variable region to serve as the basis of the reshaped human (or CDR-grafted or fully humanized) variable region is based on the extent of identity between the mouse variable region and the human variable region. If a consensus sequence is to be used as the basis of humanization, then according to the present invention, the identity should be greater than 65 to 70%.

Consensus sequences of human heavy chain variable regions are preferred for the design of reshaped human heavy chain variable regions. In the Examples, the consensus sequence for subgroup I of human heavy chain variable regions was used.

For the humanization of other antibodies, the consensus sequences for other human subgroups may be more suitable. The selected consensus sequences are usually modified at a few amino acid residues in order to recreate a fully-functional antigen-binding site. The number of amino acids changed is usually from 0 to 10% of the total number of amino acids in the variable region and, in the examples, is from 5 to 10%.

Construction and expression of chimeric 425 antibody:

Before the cDNAs coding for the VL and VH regions can be used in the construction of chimeric 425 antibody, it is necessary to introduce several modifications at the 5'- and 3'ends these include introducing appropriate restriction enzyme sites so that the variable region coding sequences can be conveniently subcloned into the HCMV expression vectors. It is necessary to re-create donor splice sites in the 3'-flanking regions so that the variable regions are spliced correctly and efficiently to the constant regions. The 5'-flanking regions are also modified to include a sequence that would create efficient initiation sites for translation by eukaryotic ribosomes (Kozak, 1987). These modifications are introduced using PCR primers. The used primers are indicated in Table 1.

TABLE 1

Oligonucleotides used for cDNA cloning, construction of chimerics, and mutagenesis. Underlined sections denote bases that anneal to the human framework.

| Number | Sequence | Description |
| --- | --- | --- |
| 1. | 5'-GTAGGATCCTGGATGGTGGGAAGATG-3' (SEQ ID NO:29) | Light chain primer for cDNA synthesis. |
| 2. | 5'-GTAGGATCCAGTGGATAGACCGATG-3' (SEQ ID NO:30) | Heavy chain primer for cDNA synthesis. |
| 3. | 5'-CTCCAAGCTTGACCTCACCATGG-3' (SEQ ID NO:31) | Chimeric $V_H$ front primer. |
| 4. | 5'-TTGGATCCACTCACCTGAGGAGACTGTGA-3' (SEQ ID NO:32) | Chimeric $V_H$ back primer. |
| 5. | 5'-AGAAAGCTTCCACCATGGATTTTCAAGTG-3' (SEQ ID NO:33) | Chimeric $V_L$ front primer. |
| 6. | 5'-GTAGATCTACTCACGTTTTATTTCCAAC-3' (SEQ ID NO:34) | Chimeric $V_L$ back primer. |
| 7. | 5'-<u>ACCATCACCTGT</u>AGTGCCAGCTCAAGTG | Reshaped $V_L$ |

TABLE 1-continued

Oligonucleotides used for cDNA cloning, construction of chimerics, and mutagenesis. Underlined sections denote bases that anneal to the human framework.

| Number | Sequence | Description |
|---|---|---|
|  | TAACTTACATGTATT<u>GGTACCAGCAG</u>-3' (SEQ ID NO:35) | CDR-1 primer. |
| 8. | 5'-CT<u>GCTGATCTAC</u>GACACATCCAACCTGGC TTCT<u>GGTGTGCCAAGC</u>-3' (SEQ ID NO:36) | Reshaped $V_L$ CDR-2 primer. |
| 9. | 5'-<u>ACCTACTACTGC</u>CAGCAGTGGAGTAGTCA-CATATTC<u>ACGTTCGGCCAA</u>-3' (SEQ ID NO:37) | Reshaped $V_L$ CDR-3 primer. |
| 10. | 5'-AGCGGTACCGACTACACCTTCACCATC-3' (SEQ ID NO:38) | Primer to introduce F71Y into $RV_L$. |
| 11. | 5'-ATACCTTCACATCCCACTG-3' (SEQ ID NO:39) | Primer to introduce S30T into $RV_H$. |
| 12. | 5'-CGAGTGGATTGGCGAGT-3' (SEQ ID NO:40) | Primer to introduce V48I into $RV_H$. |
| 13. | 5'-TTTAAGAGCAAGGCTACCATGACCGTGGA-CACCTCT-3' (SEQ ID NO:41) | Primer to introduce R66K, V67A, L71V into $RV_H$. |
| 14. | 5'-CATGACCGTGGACACCTCT-3' (SEQ ID NO:42) | Primer to introduce L71V into $RV_H$. |

For each variable region cDNA two primers are preferably designed. In the front primers, 15 bases at the 3'-end of the primer are used to hybridize the primer to the template DNA while the 5'-end of the primer contains a HindIII site and the "Kozak" sequence. The back primers have a similar design with 15 bases at the 3'-end used to hybridize the primer to the template DNA and the 5'-end of the primer contains a BamHI site and a donor splice site. In the case of the light chain back primer, a BglII site is used instead of BamHI site because the cDNA coding for the $V_L$ contains an internal BamHI site (FIG. 2). The PCR reaction is preferably carried out as described in the examples.

The PCR-modified $V_L$ region DNA is cloned into the HindIII-BamHI sites of the HCMV light chain expression vector as a HindIII-BglII fragment. This vector already contains the human genomic kappa constant region with the necessary splice acceptor site and poly($A^+$) sites. The entire PCR-modified $V_L$ fragment is sequenced using two primers that anneal to sites flanking the cloning site in the expression vector. Sequencing confirms that no errors have been incorporated during the PCR step. The PCR-modified $V_H$ DNA is cloned into the HCMV heavy chain expression vector as a HindIII-BamHI fragment and also sequenced to confirm the absence of PCR errors. A BamHI fragment containing the human genomic gamma-1 constant region is inserted into the HCMV-$CV_H$ vector on the 3'-side of the $V_H$ region. This fragment contains the necessary acceptor splice site for the V-C splice to occur in vivo and the naturally occurring poly ($A^+$) site.

The expression vectors containing the chimeric 425 $V_L$ and $V_H$ regions are co-transfected into appropriate eukaryotic cells, preferably COS cells. After approximately 72 h of transient expression, the cell culture medium is assayed by ELISA for human IgG production and for binding to EGFR protein. Amounts of human IgG detected in the media vary from 100–400 ng/ml. The chimeric antibody produced binds well to EGFR protein in a standard antigen-binding ELISA thus confirming that the correct mouse variable regions has been cloned and sequenced.

Initial design, construction and expression or reshaped human 425 light and heavy chains:

In designing a reshaped human 425 antibody, most emphasis is placed on the $V_H$ region since this domain is often the most important in antigen-binding (Amit et al., 1986; Verhoeyen et al., 1988). To select the human FRs on which to graft the mouse CDRs, the FRs of mouse MAb 425 $V_H$ region are compared with the FRs from the consensus sequences for all subgroups of human $V_H$ regions (Kabat et al., 1987). This comparison shows that the FRs of mouse MAb 425 $V_H$ are most like the FRs of human $V_H$ subgroup I showing an approximately 73% identity within the FRs and an approximately 65% identity over the entire $V_H$ regions.

A further comparison of the mouse 425 $V_H$ region with other mouse $V_H$ regions from the same Kabat subgroups is carried out to identity any FR residues which are characteristic of MAb 425 and may, therefore, be involved in antigen binding. The residue at position 94 of the mouse MAb 425 $V_H$ region is a serine while in other $V_H$ regions from mouse subgroup II (B), and also from human subgroup I, residue 94 is an arginine (Kabat et al., 1987). This amino acid substitution is an unusual one and, since position 94 is adjacent to CDR-3, it is at a surprisingly important position. For these reasons, the reshaped human 425 $V_H$ region is preferably designed based on the CDRs of mouse MAb 425 and FRs derived from the consensus sequence for human subgroup I FRs (as defined by Kabat et al., 1987). Positions 94 in FR-3 is made a serine as found in mouse MAb 425. At positions in the consensus sequence for human subgroup I FRs where no single amino acid are listed, the most commonly occurring amino acid at that position is selected. If there is no preferred amino acid at a particular position in the human consensus sequence, the amino acid that is found at that position in the sequence of mouse MAb 425 $V_H$ is selected. The resulting amino acid sequence comprises the first version (versions "a") of reshaped human 425 $V_H$ (FIG. 3). All subsequent versions of reshaped human 425 $V_H$ are modifications of this first version.

A 454 bp DNA fragment coding for the reshaped human 425 $V_H$ region, as described above, is designed and synthesized (see examples and FIG. 3). In addition to DNA sequences coding for the amino acids of reshaped human 425 $V_H$ region, this DNA fragment also contains sequences coding for a human leader sequence. The human leader sequence can be taken for example from antibody HG3 CL (Rechavi et al., 1983), a member of human $V_H$ subgroup I (Kabat et al., 1987). The synthetic DNA fragment also contains eukaryotic translation signals at the 5'-end (Kozak, 1987), a donor splice site at the 3'-end (Breathnach et al., 1978), and HindIII and BamHI sites at the 5'- and 3'-ends, respectively, for subcloning into the HCMV expression vector.

A similar procedure is carried out for the design of the reshaped human 425 $V_L$ region. The FRs of mouse MAb 425 $V_L$ region are compared with the consensus sequences for all the subgroups of human $V_L$ regions (Kabat et al., 1987). Within the FRs, an approximately 71% identity is found between mouse 425 $V_L$ and human kappa $V_L$ subgroup III, and an approximately 70% identity with human kappa $V_L$ subgroup I. DNA coding for human FRs of human kappa $V_L$ subgroup I is already available from the reshaped human D1.3 $V_L$ region (EP 239 400, Winter) and reshaped human CAMPATH-1 (Reichmann et al., 1988). The design of the reshaped human $V_L$ regions in these two human antibodies is based on the structurally-solved human immunoglobulin REI protein (Epp et al., 1975). For these reasons, the human $V_L$ FRs from reshaped human D1.3 and CAMPATH-1H are also used in reshaped human 425 $V_L$. A comparison of the FRs of mouse 425 $V_L$ region with FRs of other mouse antibodies from similar subgroups reveal no significant differences in amino acid residues at functionally important positions. No changes in the human FRs are necessary therefore. The amino acid sequence of the reshaped human 425 $V_L$ region version "a" is shown in FIG. 4.

To construct the reshaped human 425 $V_L$ region, three oligonucleotides are designed that contain internal DNA sequences coding for the three CDRs of mouse 425 $V_L$ region and also contain 12 bases at the 5'- and 3'-ends designed to hybridize to the DNA sequences coding for the human FRs in reshaped human D1.3 $V_L$ region (see oligonucleotides 7–9 in Table I). CDR-grafting is carried as described in the examples. After DNA sequencing of putative positive clones from the screening, the overall yield of the triple mutant is 5–15%, preferably 9–10%. A reshaped human 425 $V_L$ region containing no PCR errors is cloned as a HindIII-BamHI fragment into the light chain expression vector to create the plasmid HCMV-RV$_L$a 425-kappa (FIG. 1).

The two expression vectors bearing the reshaped human 425 $V_L$ and $V_H$ regions are now co-transfected into appropriate cells (see above) to look for transient expression of a functional reshaped human 425 antibody. After approximately 72 h, the cell supernatants are harvested and assayed by ELISA for human IgG. Human IgG can be detected at levels ranging from 100–500 ng/ml, however, in the ELISA assay for antigen binding, binding to EGFR is surprisingly undetectable. When the cells are co-transfected with HCMV-RV$_L$a425-kappa/HCMV-CV$_H$425 -gamma-1, human IgG is produced and it binds to EGFR. However, when cells are co-transfected with HCMV-CV$_L$425-kappa/ HCMV-RV$_H$a425-gamma-1, human IgG is produced but it does not bind to EGFR at detectable levels. From these unexpectable results, it is clear that further inventive modifications in the FRs of reshaped human 425 $V_H$ are necessary in order to get a functional antigen-binding site.

Modifications in the FRs of reshaped human 425 $V_H$ region:

Further changes in the FRs of reshaped human 425 $V_H$ region are made based on a molecular model of the mouse 425 variable region domains. The CDR loops of the reshaped human $V_H$ region are examined to see how they fit into the canonical structures described by Chothia et al., 1989. As a result of this analysis, certain changes in the FRs are made. Other changes in the FRs are made based on a functional reshaped human anti-Tac antibody that was also designed based on human FRs from subgroup I (Queen et al., 1989). Surprisingly, the $V_H$ region of mouse anti-Tac antibody is approximately 79% identical to the $V_H$ region of mouse 425 antibody. Now, according to the invention, a molecular model of the mouse 425 variable regions is made (FIG. 5). The model is based on the structure of HyHEL-5, a structurally-solved antibody whose variable regions exhibit a high degree of homology to those of mouse 425 antibody. As a result of the above analysis, amino acid residues at positions 30, 48, 67, 68 and 71 in the reshaped human 425 $V_H$ region are changed to be identical to the amino acids occurring at those positions in mouse 425 $V_H$ region. To dissect the individual effects of these changes, a variety of combinations of these changes are constructed and tested according to the invention.

In total, 8 new versions of the reshaped human 425 $V_H$ region are constructed (see FIG. 4). From the versions generated by the methods described in detail in the examples, other versions are made by recombining small DNA fragments from previous versions. Once all the desired versions are assembled preferably in pUC18, the reshaped human 425 $V_H$ regions are transferred as HindIII-BamHI fragments into the HCMV-V$_H$ expression vector thus generating versions "b" to "i" of plasmid HCMV-RV$_H$425-gamma-1 (FIG. 4).

Modifications in the FRs of reshaped human 425 $V_L$ region:

Although the corresponding cells co-transfected with vectors expressing the reshaped human 425 light chain, version "a", and chimeric 425 heavy chain do produce an antibody that bound to EGFR, the antibody with the reshaped human 425 light chain does not appear to bind as well as chimeric 425 antibody. Examination of the $V_L$ regions of mouse 425 and reshaped human 425 version "a" reveal that residue 71, which is part of the canonical structure for CDR-1 (L1), is not retained in version "a" (Chothia et al., 1989). The PCR-mutagenesis method (Kamman et al., 1989) is preferably used to introduce a Phe to Tyr change at this position. The HindIII-BamHI fragment generated from this mutagenesis is introduced into the HCMV-V$_L$ expression vector to generate HCMV-RV$_L$b425-kappa (FIG. 4).

Analysis of the new versions of reshaped human 425 $V_H$ region:

The expression vectors containing reshaped human $V_H$ versions "a" to "i" are co-transfected into the above characterized cells with the expression vector containing reshaped human $V_L$ region version "a". After about 3 days, the cell supernatants are analyzed by ELISA for human IgG production. Levels of production vary between 50–500 ng/ml. The samples are then analyzed by ELISA for human IgG capable of binding to EGFR. The different versions of reshaped human VH regions result in a wide variety of levels of antigen binding (FIG. 6). In this ELISA assay for antigen binding, the various reshaped human 425 antibodies can be directly compared with chimeric 425 antibody, but no to mouse 425 antibody. This is because the antibody used to detect binding to antigen is an anti-human IgG antibody. The nine versions of reshaped human $V_H$ region can be grouped according to their ability to bind to EGFR. Reshaped human $V_H$ region version "g" and "i" provide the highest levels of binding, followed by version "c", "f", and "h", and then followed by version "b". In some experiments, version "e" gives low, but detectable, levels of binding. Versions "a" and "d" never give detectable levels of binding. A competition binding assay is used to directly compare the reshaped human 425 antibodies containing versions "g" and "i" of $V_H$, and the chimeric 425 antibody, to mouse 425 antibody (FIG. 7). Since the antibodies in the cell supernatants are not purified and are, therefore, quantitated by ELISA, the results from the competition-binding assay are regarded as giving relative levels of binding rather than an accurate quantitation of affinity. Competition binding assays with samples from four experiments in, for example, COS cells provide consistent results with respect to relative levels of binding to antigen. Chimeric 425 antibody compete well with the labelled mouse 425 antibody and give a percent inhibition of binding just slightly less than that obtained when unlabelled mouse 425 antibody is competed with labelled mouse 425 antibody (FIG. 7, Panel A). Reshaped human antibody with $V_L$a and $V_H$g is better than that with $V_L$a and $V_H$i region (FIG. 7, Panel B). Comparison of the plateau points of the binding curves indicates that the reshaped human antibody with $V_H$g competes with labelled mouse 425 antibody 60–80% as well as the unlabelled mouse 425 antibody does in the same assay. When the results using samples from four independent experiments in, for example, COS or CHO cells were averaged, reshaped human antibody containing $V_L$a and $V_H$g give a binding that is 60–80% that of mouse 425 antibody.

Based on these results, it is possible to comment on the relative contributions of individual residues in the FRs make to antigen binding. The most significant single change in this study is the L71V change. Without this change, surprisingly, no binding to antigen is detectable (compare versions "a" and "b" of $V_H$). The R67K and V68A changes are, surprisingly, also important for binding (compare versions "b" and "c", and versions "i" and "h" of $V_H$). While introduction of V48KI change alone, and V48I and S30T together, fail to produce significant antigen binding, changes at these positions do enhance antigen binding. The S30T change, surprisingly seems to have a greater effect than the V48I change (compare versions "g" and "i", and versions "f" and "i" of $V_H$).

Analysis of the new version of reshaped human 425 $V_L$ region:

The expression vector containing the $RV_L$b425 was co-transfected into appropriate preferably eukaryotic cells with the expression vector containing reshaped human $V_H$ region versions "b", "c" or "g". Cell supernatants are harvested and assayed for human IgG production and then for human IgG capable of binding to EGFR (FIG. 8, Panel A). These results show that version "b" of reshaped human 425 $V_L$ region increases the binding to antigen. A competition binding assay is then carried out to compare reshaped human 425 antibodies with $V_L$a plus $V_H$g and $V_L$b plus $V_H$g to mouse 425 antibody. Reshaped human MAb 425 with version "b" of the $V_L$ region has a greater avidity for antigen. Thus, a F71Y change in the $V_L$ increases antigen binding. The reshaped human MAb 425 with $V_L$b and $V_H$g has an avidity for antigen greater than 60–80% of that of the murine MAb 425.

From other experiments, using a reshaped human antibody containing $V_L$b plus $V_H$g (Examples 10, 11) it can be seen, that the binding potency to EGFR is similar for chimeric, reshaped and murine antibodies.

The invention demonstrates that relatively conservative changes in the FR residues can strongly influence antigen-binding.

The molecular model of mouse 425 variable regions clearly shows this residue at position 30 in $V_H$ to be on the surface of the molecule, in the vicinity of CDR-1. In fact, H1, as defined by Chothia and Lesk, 1987, extends from residues 26 to 32, thus encompassing the residue at position 30. When the residue at position 30 is changed from Ser to Thr in the CAMPATH-1H antibody, it has no effect on antigen binding. When position 30 is changed from Ser to Thr in reshaped human $V_H$425, binding to antigen is improved. It appears that the amino acid at position 30 does play a role in antigen binding in this particular antibody-antigen interaction. Since the S30T change only improves antigen binding slightly and since the change is not essential for antigen binding, the Thr at position 30 has only a weak interaction with the antigen.

The residue change at position 71 in $V_H$ strongly influences antigen binding. This is surprising since the two residues tested at this position, Val and Leu, only differ by one methyl group. H2 of mouse 425 antibody is a member of H2, group 2 canonical structures as defined by Chothia et al., 1989. HyHEL-5 has an H2 with an amino acid sequence similar to that of the H2 of mouse 425 antibody. In HyHEL-5, a Pro at position 52A in CDR-2 packs into a cavity created by the small amino acid (Ala) at position 71 in the FRs. In the model of the mouse 425 variable regions, there is a similar interaction between Pro-52A and Val-71. Although in mouse 425 $V_H$ the Pro at position 52A is able to pack into the cavity created by Val at position 71, replacement of Val-71 with a Leu causes molecular clashing that could alter the conformation of the CDR-2 loop. For this reason, the V71L change in reshaped human VH425 re-creates the CDR-2-FR interaction as it occurs in mouse 425 $V_H$. This, surprisingly, greatly improves the antigen-binding properties of the reshaped human 425 antibodies (compare reshaped human antibodies with versions "a" and "b" of $V_H$ in FIG. 6).

The change at position 71 in $V_L$ probably affects CDR conformation because residue 71 is a member of the proposed canonical structure for L1 (CDR-1) (Chothia et al., 1989). Residue 29 in CDR-1 is a buried residue and has a contact with residue 71 in the FRs. In mouse 425 antibody, residue 71 in $V_L$ is Tyr. In the human FRs used for constructing the reshaped human $V_L$s, it is a Phe. It appears that the hydroxyl group found in Tyr, but not in Phe, has a role in maintaining the correct conformation of CDR-1.

From the molecular model of the mouse 425 variable regions, it appears that Lys-66 forms a salt bridge with Asp-86. Introduction of larger Arg residue at position 66 would disrupt the structure. Ala-67 may interact with CDR-2 and simultaneously changing residues 66 and 67 to Arg and Val, as in $V_H$a425, could have an adverse steric effect on CDR-2. The residue at position 48 is known to be buried (Chothia and Lesk, 1987), and the model confirms this. Changing residue 48 from an Ile, as found in mouse 425 antibody, to a Val, as found in human $V_H$ regions of subgroup I, could affect antigen binding by generally disrupting the structure. The amino acid at position 48 is also close to CDR-2 and may have a subtle steric effect on the CDR-2 loop.

From the competition binding studies, the best reshaped human $V_L$ and $V_H$ regions are $V_L$b and $V_H$g. $V_H$g has all 5 of the FR changes discussed above plus the change at position 94 that is included in the first version of reshaped human 425 $V_H$ region. The FRs in version "b" of reshaped human 425 $V_L$ region are 70% identical to those in mouse 425 $V_L$ region. The FRs in version "g" of reshaped human 425 $V_H$ region are 80% identical to those in mouse.

Therapeutic and diagnostic use of the antibodies:

The antibodies according to the invention can be administered to human patients for therapy or diagnosis according to known procedures. Typically the antibody, or antibody fragments, will be injected parenterally, preferably intraperitoneally. However, the monoclonal antibodies of the invention can also be administered intravenously.

Determination of appropriate titers of antibody to administer is well within the skill of the art. Generally, the dosage ranges for the administration of the monoclonal antibodies of the invention are those large enough to produce the desired tumor suppressing effect. The dosage should not be so large as to cause adverse side effects, such as unwanted cross reactions, anaphylactic reactions, and the like. Generally, the dosage will vary with the age, condition, sex and extent of the disease in the patient and can be determined by one of skill in the art. The dosage can be adjusted by the individual physician in the event of any counter indications, immune tolerance or similar conditions. Dosage can vary from 0.1 mg/kg to 70 mg/kg, preferably 0.1 mg/kg to 500 mg/kg/dose, in one or more doses administrations daily, for one or several days.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

The antibodies can be conjugated to a toxin such as ricin subunit A, diptheria toxin, or toxic enzyme. Alternatively it can be radiolabelled according to known methods in the art. However, the antibody of the present invention display excellent cytotoxicity, in the absence of toxin, in the presence of effector cells, i.e. human monocytes.

Solid tumors which can be detected and treated using the present methods include melanoma, glioma and carcinoma. Cancer cells which do not highly express EGFR-receptors can be induced to do so using lymphokine preparations. Also lymphokine preparations may cause a more homogenous expression of EGF-receptors among cells of a tumor, leading to more effective therapy.

Lymphokine preparations suitable for administration include interferon-gamma, tumor necrosis factor, and combinations thereof. These can be administered intravenously, Suitable dosages of lymphokine are 10,000 to 1,000,000 units/patient.

For diagnostic purposes the antibody can be conjugated to a radio-opaque dye or can be radiolabelled. A preferred labelling method is the Iodogen method (Fraker et al., 1978). Preferably the antibody will be administered as F(ab')$_2$ fragments for diagnostic purposes. This provides superior results so that background substraction is unnecessary. Fragments can be prepared by known methods (e.g., Herlyn et al., 1983). Generally pepsin digestion is performed at acid pH and the fragments are separated from undigested IgG and heavy chain fragments by Protein A-SEPHAROSE™ chromatography.

The reshaped human 425 antibodies according to the invention are less likely than either mouse or chimeric 425 antibodies to raise an immune response in humans. The avidity of the best version of reshaped human 425 antibody equals that of mouse or chimeric 425 antibody in the best embodiments of the invention. Binding studies show that the potency to compete with EGF for binding to EGFR under optimized conditions is the same for chimeric, reshaped and murine antibodies. Moreover, the reshaped human 425 antibodies are more efficacious, when used therapeutically in humans, than either the mouse or chimeric 425 antibodies. Due to the great reduction in immunogenicity, the reshaped human 425 antibody has a longer half-life in humans and is the least likely to raise any adverse immune response in the human patient.

The results of the defined MAb 425 show that humanized monoclonal antibodies having an artificial consensus sequence do not effect a remarkable minimum response. Further advantages are described above in the paragraph: Summary of the Invention.

Therefore, the value of the new antibodies of the invention for therapeutic and diagnostic purposes is extraordinarily high.

References cited in the specification:
Amit et al. (1986), Science 233, 747
Aviv et al. (1972), Proc. Nat. Acad. Sci. USA 69, 1408
Bernstein et al. (1977), J. Mol. Bio. 112, 525
Breathnach et al. (1978), Proc. Natl. Acad. Sci USA 75, 4853
Brooks et al. (1983), J. Comp. Chem 4, 187
Brüggemann et al. (1987), J. Exp. Med. 166, 1351
Carter et al. (1985), Oligonucleotide Sitedirected Mutagenesis in M 13, an Experimental Approach Manual, Anglian Biotechnology Ltd. Colchester
Chirgwin et al. (1979), Biochemistry 18, 5294
Chothia et al. (1987), J. Mol. Biol. 196, 901
Chothia et al. (1989), Nature 342, 877
Co et al. (1991), Proc. Natl. Acad. Sci. USA 88, 2869
Cohen (1982), J. Biol. Chem. 258, 1523
Downward et al. (1984), Nature 307, 521
Epp et al. (1975), Biochemistry 14, 4943
Epp et al. (1983), Eur. J. Biochem. 133, 51
Fraker et al. (1978), Biochem. Biophys. Res. Commun. 80, 849
Gillis et al. (1990), Hum. Antibod. Hybridomas 1, 47
Giorgi et al. (1983), Transplant. Proc. 15, 639
Gorman et al. (1991), Proc. Natl. Acad. Sci. USA 88, 4181
Gubler et al. (1983), Gene 25, 263
Hale et al. (1988), Lancet, ii, 1394
Herlyn et al. (1983), Cancer Res. 43, 2731
Hoggenboom et al. (1990), J. Immunol. 144, 3211
Jaffers et al. (1986), Transplantation 41, 572
Jones et al. (1986), Nature 321, 14
Kaariten et al. (1983), J. Immunol. 130, 937
Kabat et al. (1987), Sequences of Proteins of Immunological Interest. US Dept. Health and Human Services, US Government Printing Offices
Kammann et al. (1989), Nucleic Acids Res. 17, 5404
Koprowski et al. (1985), Somatic Cell and Mol. Genetics 11, 297
Kozak (1987), J. Mol. Bio. 196, 947
Levy et al. (1987), Gene 54, 167
Liu et al. (1987), Proc. Natl. Acad. Sci. USA 84, 3439
LoBuglio et al. (1989), Proc. Natl. Acad. Sci. USA 86, 4220
Maeda et al. (1991), Hum. Antibod. Hybridomas 2, 124
Martin (1990), D. Phil. thesis, Oxfor University
Martin et al. (1989), Proc. Natl. Acad. Sci. USA 86, 9268
Mathieson et al. (1990), N. Eng. J. Med. 323, 250

Murthy et al. (1987), Arch. Biochem. Biophys. 252, 549
Nakamaye et al. (1986), Nucleic Res. 14, 9679
Padlan et al. (1989), Proc. Natl. Acad. Sci. USA 86, 5938
Panka et al. (1988), Proc. Natl. Acad. Sci. USA 85, 3080
Queen et al. (1989), Proc. Natl. Acad. Sci. USA 86, 10029
Rabbitts et al. (1984), Curr. Top. Microbiol. Immunol. 113,
Rechavi et al. (1983), Proc. Natl. Acad. Sci. USA 80, 855
Reichmann et al. (1988), Nature 322, 21
Rodeck et al. (1987), Cancer Res. 47, 3692
Sayers et al. (1988), Nucleic Acid Res. 16, 791
Schreiber (1983), J. Biol. Chem. 258, 846
Sheriff et al. (1987), Proc. Natl. Acad. Sci. USA 84, 8075
Show et al. (1986), Proteins 1, 267
Suh et al. (1986), Proteins 1, 74
Sun et al. (1987), Proc. Natl. Acad. Sci. USA 84, 214
Sutcliffe (1988), Ph.D. thesis, London University
Takahashi et al. (1987), Cancer Res. 47, 3847
Takahashi et al. (1982), Cell 29, 671
Taylor et al. (1985a), Nucleic Acids Res. 13, 8749
Taylor et al. (1985b), Nucleic Acids Res. 13, 8764
Tempest et al. (1991), Biol. Technology 9, 266
Ulrich et al. (1984), Nature 309., 418
Verhoeyen et al. (1988), Science 239, 18
Verhoeyen et al. (1991), In Epenetos, A.A. (ed.), Monoclonal
Antibodies: Applications in Clinical Oncology, Chapman and Hall, London, pp. 37
Ward et al. (1989), Nature 341, 544
Whittle et al. (1987), Protein Eng. 1, 499
Williams et al. (1990), Tibtech 8, 256

EXAMPLE 1

Molecular cloning sequencing:

Total RNA was isolated from cell line W425–15 (ATCC HB 9629) which produces MAb 425. Approximately $9.6 \times 10^7$ cells were used to produce total RNA using the guanidinium-CsCl method (Chirgwin et al., 1979). Supernatants from the cells used for total RNA isolation were assayed by ELISA to ensure that the cells were producing the correct MAb in high amounts. Poly(A+) RNA was prepared (Aviv and Leder, 1972). Double-stranded cDNA was synthesized essentially according to the methods of Gubler and Hoffman (1983) except that primers homologous to the 5'-regions of the mouse kappa and gamma-2a immunoglobulin constant regions were used to prime first-strand synthesis (Levy et al., 1987). The design of the light chain primer was a 26-mer (oligonucleotide 1, Table I) (SEQ ID NO:29 which was designed based on published data (Levy et al., 1987; Kaariten et al., 1983). The design of the heavy chain primer was a 25-mer (oligonucleotide 2, Table I) (SEQ ID NO: 30) and designed based on published data (Kaariten et al., 1983; Kabat et al., 1987). Primers were designed and synthesized on an Applied Biosystems 380B DNA Synthesizer and purified on urea-acrylamide gels. After second-strand synthesis, the blunt-ended cDNAs were cloned into SmaI-digested pUC18 (commercially available) and transformed into competent *E. coli* cells, e.g. DH5-alpha (commercially available). Colonies were gridded onto agar plates and screened by hybridization using $^{32}$P-labelled first-strand synthesis primers (Carter et al., 1985). Sequencing of double-stranded plasmid DNA was carried out using Sequence (United States Biochemical Corporation).

EXAMPLE 2

Construction of chimeric genes:

For each variable region, a front 5' and back 3' polymerase chain reaction (PCR) primer was synthesized (oligonucleotides 3–6, Table I). PCR reactions were set up using 1 ng of pUC18 plasmid DNA containing the cloned cDNA, front and back PCR primers at a final concentration of 1 μM each, 200 μM of each dNTP, 10 mM Tris-HCl (pH 8.3), 50 mM KCl, 1.5 mM MgCl, and 0.01% gelatin (w/v). Amplitaq DNA polymerase (Perkin Elmer Cetus) was added at 2.5 units per assay. After an initial melt at 94° C. for 1.5 min, 25 cycles of amplification were performed at 94° C. for 1 min, 45° C. for 1 min, and 72° C. for 3 min. A final extension step at 72° C. was carried out for 10 min. PCR reactions were phenol/chloroform extracted twice and ethanol precipitated before digesting with HindIII and BamHI. The PCR fragment coding for the $V_L$ or $V_H$ region was then cloned into an expression vector. This vector contains the HCMV (human cytomelovirus) enhancer and promoter, the bacterial neogene, and the SV40 origin of replication. A 2.0 Kb BamHI fragment of genomic DNA coding for the human gamma-1 constant region (Takahashi et al., 1982) was inserted in the correct orientation downstream of the $V_H$ region fragment (see HCMV-CV$_H$425-gamma-1 in FIG. 1). This vector was later adapted by removing the BamHI site at the 3'-end of the constant region fragment thus allowing variable regions to be directly inserted into the heavy chain expression vector as HindIII-BamHI fragments (Maeda et al., 1991). The fragment coding for the $V_L$ region was inserted into a similar HCMV expression vector, in this case containing a BamHI fragment of genomic DNA, approximately 2.6 Kb in size, coding for the human kappa constant region and containing a splice acceptor site and a poly(A+) (Rabbitts et al., 1984) (see HCMV-CV$_L$-425-kappa in FIG. 1).

EXAMPLE 3

Molecular modelling of MAb 425 $V_L$ and $V_H$:

A molecular model of the variable regions of murine MAb 425 was built on the solved structure of the highly homologous anti-lysozyme antibody, HyHEL-5 (Sheriff et al., 1987). The variable regions of MAb 425 and HyHEL-5 have about 90% homology.

The model was built on a Silicon Graphics Iris 4D workstation running UNIX and using the molecular modeling package "QUANTA" (Polygen Corp.). Identical residues in the framework were retained; non-identical residues were substituted using the maximum overlap (Snow and Amzel, 1986) incorporated into QUANTA's protein modeling facility. The main chain conformation of the three N-terminal residues in the heavy chain were substituted from a homologous antibody structure (HyHEL-10 (Padlan et al., 1989)) since their temperature factors were abnormally high (greater than the mean plus three standard deviations from the backbone temperature factors) and since they influence the packing of $V_H$ CDR-3 (H3) (Martin, 1990). The CDR-1 (L1) and CDR-2 (L2) sequences of the $V_L$ region and the CDR-1 (H1) and CDR-2 (H2) sequences of the $V_H$ region from MAb 425 corresponded to canonical forms postulated by Chothia et al. (1989). The main chain torsion angles of these loops were kept as in HyHEL-5. The CDR-3 (L3) sequence of the $V_L$ region and the CDR-3 (H3) of the $V_H$ region from MAb 425 did not correspond to canonical structures and, therefore, were modeled in a different way. The computer program of Martin et al. (1989) was used to extract loops from the Brookhaven Databank (Bernstein et al., 1977). The loops were then sorted based on sequence similarity, energy, and structure-determining residues (Sutcliffe, 1988). The top-ranked loops were inspected on the graphics and the best selected by eye. H3 was modeled on bovine glutathione peroxidase (Epp et al., 1983) in the region of residues 92–103. L3 was modelled on the murine IgA (J539) Fab fragment (Suh et al., 1986) in the region of residues 88–96 of the light chain.

The model was subjected to steepest descents and conjugate gradients energy minimization using the CHARm potential (Brooks et al., 1983) as implemented in QUANTA in order to relieve unfavorable atomic contacts and to optimize Van der Waals and electrostatic interactions.

EXAMPLE 4

Construction of humanized antibody genes:

The construction of the first version of the reshaped human 425 light chain was carried out using a CDR-grafting approach similar to that described by Reichmann et al. (1988) and Verhoeyen et al. (1988). Single-stranded template DNA was prepared from a M13mp18 vector (commercially available) containing a HindIII-BamHI fragment coding for the human anti-lysozyme $V_L$ region (EP 239 400, G. Winter). The FRs of this light chain are derived from the crystallographically-solved protein REI. Three oligonucleotides were designed which consisted of DNA sequences coding for each of the mouse MAb 425 light chain CDRs flanked on each end by 12 bases of DNA complementary to the DNA sequences coding for the adjacent FRs of human REI (oligonucleotides 7–9 in Table I (SEQ ID NO: 35–37). Oligonucleotides were synthesized and purified as before. All three oligonucleotides were phosphorylated and used simultaneously in an oligonucleotide-directed in vitro mutagenesis system based on the methods of Eckstein and coworkers (Taylor et al., 1985; Nakamaye and Eckstein, 1986; and Sayers et al., 1988). The manufacturer's instructions were followed through the exonuclease III digestion step. The reaction was then phenol/chloroform extracted, ethanol precipitated, and resuspended in 100 μl of TE. A volume of 10 μl was used as template DNA in a 100 μl PCR amplification reaction containing M13 universal primer and reverse sequencing primer to a final concentration of 0.2 μM each. Buffer and thermocycling conditions were as described in Example 2 with the exception of using a 55° C. annealing temperature. The PCR reaction was phenol/chloroform extracted twice and ethanol precipitated before digestion with HindIII and BamHI and subcloning into pUC18. Putative positive clones were identified by hybridization to $^{32}$P-labelled mutagenic primers (Carter et al., 1987). Clones were confirmed as positive by sequencing. A $V_L$ region containing all three grafted CDRs was cloned as a HindIII-BamHI fragment into the $V_L$ expression vector to create the plasmid HCMV-RV$_L$a425-kappa.

Version "b" of the reshaped $V_L$ was constructed using the PCR mutagenesis method of Kammann et al. (1989), with minor modifications. The template DNA was the RV$_L$a subcloned into pUC18. The first PCR reaction was set up in a total volume of 50 μl and contained 1 ng template, M13 reverse sequencing primer and primer 10 (Table I) at a final concentrations of 1 μM, 200 μM dNTPs, 10 mM Tris-HCl (pH 8.3), 50 mM KCl, 1.5 mM MgCl, and 0.01% (w/v) gelatin. Amplitag DNA polymerase was added at a concentration of 1 unit per assay. The reaction was set up in triplicate. After melting at 94° C. for 1.5 min, the reactions were cycled at 1 min 94° C., 1 min 37° C., and 2 min 72° C. for 40 cycles, followed by an extension at 72° C. for 10 min. The reactions were pooled, phenol/chloroform extracted and ethanol precipitated before isolating the PCR product from a TAE agarose gel. A tenth of the first PCR reaction was then used as one of the primers in the second PCR reaction. The second reaction was as the first except the first reaction product and 20 pmol of M13 universal primer were used. Cycling was as described by Kammann et al. (1989). The HindIII-BamHI fragment was cloned into pUC18 and sequenced. A DNA fragment bearing the desired change was subcloned into the $V_L$ expression plasmid to create plasmid HCMV-RV$_L$b425-kappa.

The first version of the reshaped human $V_H$ region of 425 was chemically synthesized. A DNA sequence was designed coding for the required amino acid sequence and containing the necessary flanking DNA sequences (see above). Codon usage was optimized for mammalian cells with useful restriction enzyme sites engineered into the DNA sequences coding for FRs. The 454 bp was synthesized and subcloned into pUC18 as an EcoRI-HindIII fragment. A HindIII-BamHI fragment coding for the reshaped humanized 425 heavy chain was then transferred into the $V_H$ expression vector, to produce the plasmid HCMV-RV$_H$a-425-gamma-1.

Eight other versions of the reshaped humanized heavy chains were constructed by a variety of methods. The HindIII-BamHI fragment coding for the version "a" of the heavy chain was transferred to M13mp18 and single-stranded DNA prepared. Using oligonucleotides 11–13 (Table I), PCR-adapted M13 mutagenesis, as described above, was used to generate DNA coding for reshaped human 425 $V_H$ regions versions "d", "e", "f" and "g" in pUC18. These versions were subcloned into the heavy chain expression vector as HindIII-BamHI fragments to create plasmids HCMV-RV$_H$d425-gamma-1, HCMV-RV$_H$e425-gamma-1, HCMV-RV$_H$f425-gamma-1, and HCMV-RV$_H$g425-gamma-1.

Reshaped human 425 $V_H$ regions versions "b" and "c" were generated using the PCR mutagenesis method of Kammann et al. (1989) as described above. The template DNA was reshaped human 425 $V_H$ region version "a" subcloned into pUC18, and the mutagenic primer used in the first PCR reaction was either primer 13 or 14 (Table I). After mutagenesis and sequencing, sequences bearing the desired changes were subcloned into the heavy chain expression plasmid to create plasmids. HCMV-RV$_H$b 425-gamma-1 and HCMV-RV$_H$c425-gamma-1.

Reshaped heavy chain versions "h" and "i" were constructed from the pUC-based clones of existing versions. A 0.2 Kb HindIII-XhoI fragment from version "e" was ligated to a 2.8 Kb XhoI-HindIII fragment from either version "b" or "c" producing the new versions "h" and "i", respectively, The HindIII-BamHI fragments coding for these versions were subcloned into the heavy chain expression vector to produce the HCMV-RV$_H$h425-gamma-1 and HCMV-RV$_H$i425-gamma-1.

EXAMPLE 5

Transfection of DNA into COS cells:

COS cells were electroporated with 10 μg each of the expression vectors bearing the genes coding for the heavy and light chains. Briefly, 10 μg of each plasmid was added to a 0.8 ml aliquot of a 1×10$^7$ cells/ml suspension of COS cells in PBS. A BIO-RAD™ Gene Pulser was used to deliver a pulse of 1900 V, with a capacitance of 25 μF. The cells were left to recover at room temperature for 10 min before plating into 8 ml DMEM containing 10% fetal calf serum. After 72 h incubation, the media was collected, centrifuged to remove cellular debris, and stored under sterile conditions at 4° C. for short periods, or at −20° C. for longer periods, prior to analysis by ELISA.

EXAMPLE 6

The transfection of DNA into CHO cells was done according to Example 5.

EXAMPLE 7

Quantification of IqG production and detection of antigen binding:

Human IgG present in COS cell supernatants was detected by ELISA: In the ELISA assay for human IgG, 96-well plates were coated with goat anti-human IgG (whole molecule) and human IgG in the samples that bound to the plates was detected using alkaline phosphatase-conjugated goat anti-human IgG (gamma-chain specific). Purchasable purified human IgG was used as a standard. Binding to the antigen recognized by MAb 425 was determined in a second ELISA. Plates were coated with an EGFR protein preparation (obtainable, for example, according to Rodeck et al., 1980) and antibodies binding to EGFR were detected using either an anti-human IgG (gamma-chain specific) peroxidase conjugate (for chimeric and reshaped human antibodies) or an anti-mouse IgG (whole molecule) peroxidase conjugate (for the mouse MAb 425 antibody) (both conjugates supplied by Sigma). Purified murine MAb 425 was used as a standard.

EXAMPLE 8

Competition binding assay:

Murine MAb 425 was biotinylated using a correspondingly purchasable kit. ELISA plates were coated with an optimal dilution of the EGFR protein. Dilutions of the COS cell supernatants, in a volume of 50 μl, were mixed with 50 μl of the biotinylated murine MAb 425 (estimated by ELISA to be 1.75 μg/ml). Each COS cell supernatant was tested in duplicate. Plates were incubated at room temperature, overnight. Bound biotinylated murine MAb 425 was detected by the addition of a purchasable streptavidin horseradish peroxidase complex. A control with no competitor present allowed a value of percentage of inhibition or blocking to be calculated for each COS cell supernatant as follows:

$$100-[(OD_{450} \text{ of sample}/OD_{450} \text{ of control}) \times 100]$$

EXAMPLE 9

Different probes of murine, reshaped and chimeric MAb 425 were analyzed by SDS-Polyacrylamide-Gelspaceelectrophoresis (SDS-PAGE) according to Laemmli et al. 2.5 μg of each sample were applied to each well under non-reducing as well as under reducing conditions. Protein was visualized by Coomassie staining. Analysis of reshped, chimeric and murine MAbs 425 by SDS-PAGE under non-reducing and under reducing conditions shows that the samples have similar purity.

MW range of the antibodies: 180,000–200,000.

EXAMPLE 10

Reshaped MAb 425 was purified by gelspacefiltration on SUPEROSE 12™ (Pharmacia Corp. Sweden) (SUPEROSE 12 consists of Protein A coupled to beaded, cross-linked agarose with an average particle size of 10 to 12 μm.) according to standard methods. The antibody was eluted with PBS (pH 7.4, 0.8 M NaCl) (0.1M). A single peak (at 5 min) can be obtained (FIG. 9).

EXAMPLE 11

Biotin-labelled MAb 425 was Used to compete with unlabelled MAb 425 or derivates for binding to EGFR. Biotin-labelling occurred according to standard methods. EGFR was solubilized from A431 membranes by standard methods. A431 cells were commercially purchased. Detection was done after incubation with POD-conjugated streptavidin and substrate. From this data inhibition curves were constructed (FIG. 10). The curves show that the binding of the various antibodies are comparable.

EXAMPLE 12

Different probes of purified murine, chimeric and reshaped MAbs 425 were tested for their potency to compete with EGF regarding their binding to EGFR. The test was performed by competing $^{125}$I-labelled EGF (Amersham Corp., GB) and various antibodies for binding to EGF-receptor positive membranes (A431). The test system is based on SPA technology (Amersham). The competition curves of the murine and the reshaped antibodies (3 probes) are nearly identical (FIG. 11).

---

We claim:

1. A humanized antibody, comprising a variable region and a constant region, wherein the hypervariable region of the light chain CDRs has the following amino acid sequences:

| | |
|---|---|
| CDR-1 | Ser—Ala—Ser—Ser—Ser—Val—Thr—Tyr—Met—Tyr (SEQ ID NO:1), |
| CDR-2 | Asp—Thr—Ser—Asn—Leu—Ala—Ser (SEQ ID NO:2) and |
| CDR-3 | Gln—Gln—Trp—Ser—Ser—His—Ile—Phe—Thr (SEQ ID NO:3); | the hypervariable region of the heavy chain CDRs has the following amino acid sequences:

| | |
|---|---|
| CDR-1 | Ser—His—Trp—Met—His (SEQ ID NO:4), |
| CDR-2 | Glu—Phe—Asn—Pro—Ser—Asn—Gly—Arg—Thr—Asn—Tyr—Asn—Glu—Lys—Phe—Lys—Ser (SEQ ID NO:5) and |
| CDR-3 | Arg—Asp—Tyr—Asp—Tyr—Asp—Gly—Arg—Tyr—Phe—Asp—Tyr (SEQ ID NO:6); | the light chain framework region has the following amino acid sequences:

| | |
|---|---|
| FR-1 | Asp—Ile—Gln—Met—Thr—Gln—Ser—Pro—Ser—Ser—Leu—Ser—Ala—Ser—Val—Gly—Asp—Arg—Val—Thr—Ile—Thr—Cys (SEQ ID NO:7), |
| FR-2 | Trp—Tyr—Gln—Gln—Lys—Pro—Gly—Lys—Ala—Pro—Lys—Leu—Leu—Ile—Tyr (SEQ ID NO:8), |
| FR-3 | Gly—Val—Pro—Ser—Arg—Phe—Ser—Gly—Ser—Gly—Ser—Gly—Thr—Asp—Xaa$_1$—Thr—Phe—Thr—Ile—Ser—Ser—Leu—Gln—Pro—Glu—Asp—Ile—Ala—Thr—Tyr—Tyr—Cys (SEQ ID NO:9) and |
| FR-4 | Phe—Gly—Gln—Gly—Thr—Lys—Val—Glu—Ile—Lys (SEQ ID NO:10); | the heavy chain framework region has the following amino acid sequences:

| | |
|---|---|
| FR-1 | Gln—Val—Gln—Leu—Val—Gln—Ser—Gly—Ala—Glu—Val—Lys—Lys—Pro—Gly—Ala—Ser—Val—Lys—Val—Ser—Cys—Lys—Ala—Ser—Gly—Tyr—Thr—Phe—Xaa$_2$ (SEQ ID NO:11), |
| FR-2 | Trp—Val—Xaa$_3$—Gln—Xaa$_4$—Xaa$_5$—Gly—Gln—Gly—Leu—Glu—Trp—Xaa$_6$—Gly (SEQ ID NO:12), |
| FR-3 | Xaa$_7$—Xaa$_8$—Thr—Met—Thr—Xaa$_9$—Asp—Thr—Ser—Thr—Asn—Thr—Ala—Tyr—Met—Xaa$_{10}$—Leu—Ser—Ser—Leu—Arg—Ser—Glu—Asp—Thr—Ala—Val—Tyr—Tyr—Cys—Ala—Ser (SEQ ID NO:13) and |
| Fr-4 | Trp—Gly—Gln—Gly—Thr—Leu—Val—Thr—Val—Ser—Ser (SEQ ID NO:14); | wherein Xaa$_1$ is Tyr, Phe, Trp or His; Xaa$_2$ is Thr or Ser; Xaa$_3$ is Arg or His; Xaa$_4$ is Ala, Lys or His; Xaa$_5$ is Pro or Val; Xaa$_6$ is Ile, Val or Leu; Xaa$_7$ is Lys, Arg or His; Xaa$_8$ is Ala, Val, Pro or Gly; Xaa$_9$ is Val, Ala, Pro or Gly; and Xaa$_{10}$ is Glu or Asn; and wherein said humanized antibody binds to human EGF receptors, and inhibits binding of EGF to EGF-receptor.

2. A humanized antibody of claim 1, wherein the constant region of the heavy chain comprises the amino acid sequence of gamma-1 chain of a human immunoglobulin.

3. A humanized antibody of claim 1, wherein the constant region of the light chain comprises the amino acid sequence of a kappa chain of a human immunoglobulin.

4. A humanized antibody of claim 1, wherein the constant region of the heavy chain comprises the amino acid sequence of gamma-1 chain, and the constant region of the light chain comprises the amino acid sequence of a kappa chain of a human immunoglobulin.

5. An expression vector, comprising a DNA encoding a variable and constant region of the heavy chain of an antibody of claim 1.

6. An expression vector, comprising a DNA encoding a variable and constant region of the heavy chain of an antibody of claim 2.

7. An expression vector, comprising a DNA encoding a variable and constant region of the heavy chain of an antibody of claim 3.

8. An expression vector, comprising a DNA encoding a variable and constant region of the heavy chain of an antibody of claim 4.

9. An expression vector, comprising a DNA encoding a variable and constant region of the light and heavy chains of an antibody of claim 1.

10. An expression vector, comprising a DNA encoding a variable and constant region of the light and heavy chains an antibody of claim 2.

11. An expression vector, comprising a DNA encoding a variable and constant region of the light and heavy chains of an antibody of claim 3.

12. An expression vector, comprising a DNA encoding a variable and constant region of the light and heavy chains of an antibody of claim 4.

13. A pharmaceutical composition comprising a humanized antibody of claim 1 and a pharmaceutically acceptable excipient.

14. A pharmaceutical composition comprising a humanized antibody of claim 2 and a pharmaceutically acceptable excipient.

15. A pharmaceutical composition comprising a humanized antibody of claim 3 and a pharmaceutically acceptable excipient.

16. A pharmaceutical composition comprising a humanized antibody of claim 4 and a pharmaceutically acceptable excipient.

17. The expression vector pRVH425 (DSM 6339).

18. A host cell transformed with the expression vector of claim 17.

19. A host cell transformed with the expression vector of claim 17 and the expression vector pRV$_L$425 (DSM 6340).

20. A host cell transformed with an expression vector of claim 5.

21. A host cell transformed with an expression vector of claim 9.

22. A method of diagnosing the presence of EGF receptor-bearing tissue, comprising contacting said tissue with a humanized antibody of claim 1 conjugated with a detectable moiety and detecting the presence of said antibody bound to said tissue.

* * * * *